US008841089B2

(12) United States Patent
Frey et al.

(10) Patent No.: US 8,841,089 B2
(45) Date of Patent: Sep. 23, 2014

(54) POLYNUCLEOTIDES FOR ENHANCING EXPRESSION OF A POLYNUCLEOTIDE OF INTEREST

(75) Inventors: Manfred Frey, Mannheim (DE); Heiko Flammann, Mannheim (DE); Mathias Hafner, Mannheim (DE)

(73) Assignee: Hochschule Mannheim, Mannheim (DE)

( * ) Notice: Subject to any disclaimer, the term of this patent is extended or adjusted under 35 U.S.C. 154(b) by 252 days.

(21) Appl. No.: 12/593,240

(22) PCT Filed: Mar. 28, 2008

(86) PCT No.: PCT/EP2008/053716
§ 371 (c)(1),
(2), (4) Date: Nov. 20, 2009

(87) PCT Pub. No.: WO2008/116931
PCT Pub. Date: Oct. 2, 2008

(65) Prior Publication Data
US 2010/0113574 A1    May 6, 2010

(30) Foreign Application Priority Data
Mar. 28, 2007    (EP) .................................... 07105109

(51) Int. Cl.
*C12P 21/00* (2006.01)
*C12N 15/85* (2006.01)
*C12N 9/12* (2006.01)
*C12P 21/06* (2006.01)
*C12P 21/04* (2006.01)
*C12N 5/00* (2006.01)
*C12N 5/02* (2006.01)
*C12N 5/07* (2010.01)
*C12N 5/10* (2006.01)
*C12N 15/00* (2006.01)
*C07H 21/00* (2006.01)
*C07H 21/02* (2006.01)
*C07H 21/04* (2006.01)
*A61K 48/00* (2006.01)

(52) U.S. Cl.
CPC .............. *C12N 9/1205* (2013.01); *C12N 15/85* (2013.01); *A61K 48/00* (2013.01); *A01K 2217/00* (2013.01); *C12N 2830/46* (2013.01); *C12N 9/12* (2013.01)
USPC ........ 435/69.1; 435/70.1; 435/70.3; 435/325; 435/358; 435/392; 435/320.1; 536/22.1; 536/23.1; 536/24.1; 536/24.2

(58) Field of Classification Search
None
See application file for complete search history.

(56) References Cited

U.S. PATENT DOCUMENTS

| 7,344,886 B2 * | 3/2008 | Enenkel et al. ............... 435/455 |
| 7,732,181 B2 * | 6/2010 | Enenkel et al. ............... 435/194 |
| 2005/0106580 A1 * | 5/2005 | Enenkel et al. ................... 435/6 |

FOREIGN PATENT DOCUMENTS

| EP | 1 676 916 | 7/2006 |
| WO | WO-02/24930 | 3/2002 |
| WO | WO 03/057146 | * 7/2003 |
| WO | WO-2004/050884 | 6/2004 |
| WO | WO-2005/040377 | 5/2005 |

OTHER PUBLICATIONS

Zahn-Zabal et al, (J Biotechnol., 2001, 87(1):29-42).
Kalos and Fournier (Mol Cell Biol., 1995, 15(1):198-207).
Klehr et al. (Biochemistry, 1991, 30(5)1264-70).
Dang et al (J Virol., 2000, 74(6):2671-8).
T. Omasha, Journal of Bioscience and Bioengineering (2002) 94, 600-605.
Hodgetts, Current Opinion in Genetics & Development (2004) 14 680-685.
Lauber et al. J Biol Chem. Sep. 26, 1997:272(39):24657-65.
Van Leeuwen et al. Plant Mol Biol. Nov. 2001;47(4):543-54.
Mol Cells. Feb. 28, 2002;13(1):61-8.
Kaul-Ghanekar et al. Nucleic Acids Res. Sep. 15, 2004;32(16):486275.
Singh et al. Nucleic Acids Research, 1997, 25(7): 1419-1425.
Fiorini et al., Biochemistry (Moscow), 2006, 71(5): 481-488.
GenBank L23999.1, GI: 398042, 1994.
Romig et al., 1994, Eur J Biochem. 221:411-419.
Girod et al. Biotechnol Bioeng. Jul. 5, 2005;91(1):1-11.
Haran et al., 1994, Sequence elements responsible for DNA curvature. J Mol Biol, 244: 135-143.
Shpigelman et al, 1993, Comput Appl Biosci.;9(4):435-40.
Sauter and Enekel, Biotechnology and Bioengineering, 89, (2005) 530-538.
Database Medline, US National Library of Medicine, Bethesda, MD, Nov. 2005, Huang Hui-Zhen et al. (Isolation and functional analysis of tobacco Mars) Database accession No. NLM16468355 & Sheng Wu Gong Cheng Xue Bao= Chinese Journal of Biotechnology Nov. 2005, vol. 21, No. 6, Nov. 2005.
Halweg, Christopher et al.: The rb7 matrix attachment region increases the likelihood and magnitude of transgene expression in tobacco cells: A flow cytometirc study Plant Cell, vol. 17, No. 2, Feb. 2005, p. 418-429.

(Continued)

*Primary Examiner* — Celine Qian
*Assistant Examiner* — Nancy J Leith
(74) *Attorney, Agent, or Firm* — Birch, Stewart, Kolasch & Birch, LLP

(57) ABSTRACT

The present invention relates to polynucleotides comprising a first nucleic acid sequence for a chromatin element, which is capable of enhancing expression, and at least one second nucleic acid sequence comprising a curved origin motif. Furthermore, the invention relates to a host cell, a non-human transgenic organism, a vector and a kit comprising the aforementioned polynucleotide. Moreover, the invention relates to methods for expressing a polynucleotide of interest.

9 Claims, 7 Drawing Sheets

(56) References Cited

OTHER PUBLICATIONS

Figure 3:
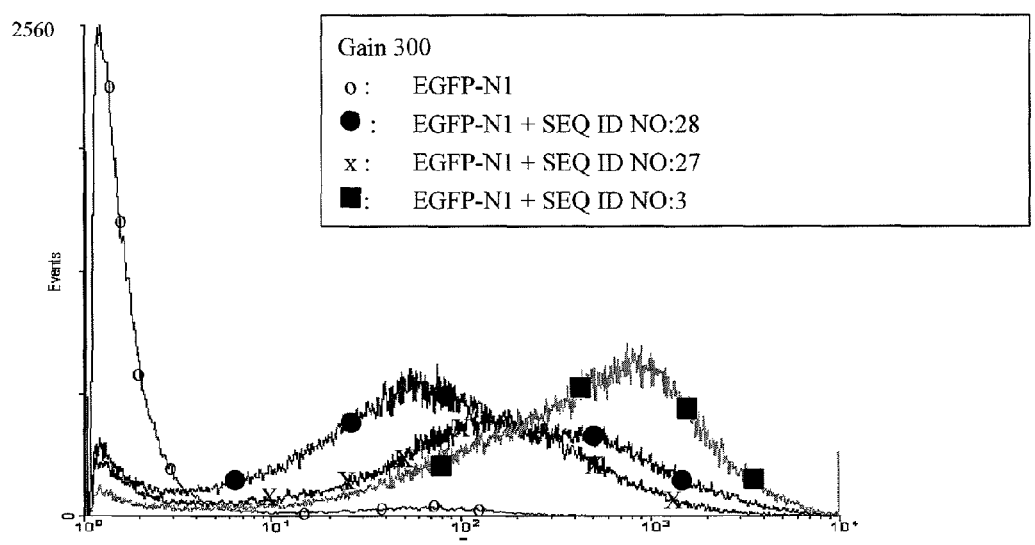

Han K-H et al.: Matrix Attachment Regions (MARS) enhance transformation frequency and transgene expression in popular, Transgenic Research, London, vol. 6, 1997, p. 415-420.

Liebich et al.:Evaluation of sequence motifs found in scaffold/matrix-attached regions (S/MARs), Nucleic Acid Research, vol. 30, No. 15, Aug. 1, 2002, p. 3433-3442.

Yamamura et al.: Analysis of sequence-dependent curvature in matrix attachment regions, FEBS Letters, Elsevier; Amsterdam, vol. 489, noi 2-3, Feb. 2, 2001, p. 166-170.

Database EMBL, Nov. 8, 2996, 3B_009_H03_FM2 *Triticum aestivum* chromosome 3B-specific BAC library (TA3B) *Triticum aestivum* genomic clone 3B_009_H03, genomic survey sequence. Database accession No. DX3666510.

Database EMBL May 3, 2002, *Parastichopus californicus* clone Psc5 microsatellite sequence. Database accession No. AF455033.

Database EMBL Sep. 10, 1993, *Homo sapiens* topoisomerease I (TOP1) gene, intron 13 fragment. Database accession No. L23999.

Database EMBL, Nov. 9, 2005, Novel compositions and methods for cancer. Database accession No. DD159111.

Database EMBL, Nov. 26, 2008, Novel compositions and methods for cancer. Database accession No. DL235650.

\* cited by examiner

Fig. 1

```
GGATCCCAATAGGAGTCATTAAAGGCCTGGAAAAGTGGTGCCATTAGGAGAAAAAGAAATGATTT
CTTGAGCTTGCTCTCAGTTCTCTTTTAGGCTGTCTTGTACTCAGCAGAATAGTGAGATCTTCAAAGG
TTGGGGTTTGATAGTGCCTTGAATAATTTTTAACTTTATATTGCCAGCGGAAGAAGCATTCTCTTTT
TAGATTTAAAAAATGTAGATACAAATATTAGGGGTTTTATTTTTAGTGAAACATTTCAAACATACA
GGAATAGATAATTATGTAATGAACACTCGTATGTCCACCATCTGGCTTTGTAAAATCTTAAAATTAT
GTCTTATGTGCTCAATTGTTTTATTTCATAAAAGATACTGATAAACATAGCTGAAGTCACTTGTATA
CCATTCACCTTCTTCCCTGTAGATTACTATGAACTCGGTCTTTTTATTCTCATACATATTTTTTGTATT
TTTGCAGTATATTTATGTGTTCATAAACAATATGTAATTTTACAATATGTAACACACTAGTAACATA
CTAATTTAAAACTTGTTTTTAGTTTACAATATGTTGTAAACTATTGTAAGCTAAAGACATATTGTAC
AACCTATTGTTAAATAAAAACAGGTTTTAGTTTTAAATTAGGTATGTTACTGGGATCATTCTGCAAC
TTGTTTATTCCTCTCCAGCTTTGATTTTGTGGTTTTATTATCTTAACCTACACTTTTAATTAATCCATT
TTATTTGTTACATGGTATTCTATTATATCATAAAAACTTATCTATTCTGTTGGTTTTTGTTGTTGGTC
ATTTGAGACCATGTCTTCGCTCTGTCACCCAGGCTGGAGTACAGTGGCGTGATCTTGGCTCACTGTG
ACCTCTGCCTCCCGGATTCAAGTGGTTTTGGTGCCTCAGCCTCCTGAGTAGCTGGGATTATAGGCGT
GTGCCACCATGCCCAGCTAATTTTTGTATTTTTAATAGAGACGGGATTTCACCATGTTGGCCAGGCT
GGTCTTGAACTGACCTCAAGTGATCTGCTCACCTCAGCTGCACAAAGTGCTGGGATTACAGGTGTT
AGCCAACCAATACCCTGCCTCTATTCTCTTGTTAAGAGGCATTTAGCATGGTTAATACAGTCTCTTG
CCCTCATAAACAGTGCTGGGAAGGAAACACATGTTCTTGTGTATATTGAATGAAATTTGTTTATAC
ATTAGATATTTCCAAATGTTCTCTTTAAGTACTTCAGTTTACATCATTACTCTCCTCCTCCCTCCCCT
CCCACCCCCACCCACAACAGTATTCCTCTTTTTCCATATCCTTGCTAATGTTTCAAAGTTTTGCTTTT
TACATTTGGGTCTTAGATCCACTAGAATGTATTTTTGCATTGGGATGAAGTTGAAACCTAATATATT
TTCCAAATGAGTAAACTGTTGTCACAGAACTATTTAGTTGTATTACCTCCTCTCTTGTATATCAGAT
ATATCTACATATATGTCAGACTGTTTCTGGGCTGTCTGTCCTCTTTAATTAGTTCGTGTATCTGTTTC
TGCATCAGTAGCATACTGTCTTAACTACTGTAGCTTTATAAAGTCTATTGAGTAGGACAAGTTTGTT
TCATTCTTCAAAATTGCTTTGGCTATTCTTGGCCCTCTGCTGTTTCATATTAACTTTCAGATAAACTT
GTCAAATTCTAATGAAAACTGTTGATAAACTTGTTGATTAACAAATTCTAATAAAAACTGTTGAGA
TTTTTATTGGAATTGCAATACATTTATAGATTAACGGAGAAAGATATTGACAATACAATTGAGTTTC
CAATTCACGAACATGTTATACCTCTCCATTAATTCATGTCTTTTGAATGTATCCACCAATATGGTTTT
GTAATTTTCTTCATAAAGGACATTTAAAATTCTTATTTTAAGTGATCTTATAGTTTTATGCTAACGTG
AATGAGATTTTTCCATTATGTTTCTGTTGGTTATTCCTGAAGTGGTAATGCTTATAATTTTGGGGTGT
TGGTCTTGTATCTGCCTAGGAGCTCGATTTTAGCTCGATTTTAGCTCGATTTTAGCTCGATTTTAGCT
CGATTTTAGCTCGATTTTAGCTCGATTTTAGCTCGATTTTAGCTCGATTTTAGCTCGATTTTAGCTCG
ATTTTAGCTCGATTTTAGCTCGATTTTAGCTCGATTTTAGCTCGATTTTAGCTCGATTTTAGCTCGAT
TTTAGCTCGATTTTAGCTCGATTTTAGCTCGATTTTAGCTCGATTTTAGCTCGATTTTAGCTCGACTC
GAGCCTAGGAGATACAAGAGGTGCTCAGAGTTGTTCAGGGTTGCTGAACTCTTAGTTCTAAAAGTG
TCTGTCATTTGGGGTTTCTATGTAGATAATTTAATTATCTATAAAAACAGTTCTTCATTTTCAGTTCA
TATATTTCATATTTTCTTAAGTTTTAATTTTTATTTTTAAACACAATTATCCATAAACCCTAACCCTT
TCCCTAGTCAACAGCAGTCACAGCCAAATGTTTTATTAATTGCTATACTCAGTGTTTCTTGTATCTC
ATACCTTCTGGGGTTTCTTGTCTTGTTGAAATACACCCTTTAATGTTTCTTTAGTGAAGACCCAACA
GTGGCACTCACTCACCTTTGTTTACCTGAAAATTTCTTTATTTTCATCTTAATTCATAGTCTGTCTTTT
CTCCAGTCAAGGAAGTGTCTTATAGGGAAGATTCTGGTTTCACTATCGTGTATCCAGGATATATATG
TATTTATAGATAGACTTTTAATCTGAGGACTAATGTATTTTATCCTACAGTATTACCAATCATTATTT
CTTCCATAACTTCTAGACCATTCCTTTTGTACTTCTTTTTTAGAGTCCTTATTAGATGAGTGTTGACT
CTTTTCAATCTAGACATCTTTTTTAAACTATATTTTCATACTCTTTGTCTCTTTAGGTCTGATTTTTA
AGTTCAGGGGATATTTCATTTTGGGTGAGTTGTAGCACTACTTCAATTCACTAATTCTAATTATATT
TAATCTACAAGTTATTCCATCTATAATTTATTTCAATTACCACTTTTTGTTTTCAAAATTTCTAATTTT
ATATCTGATTTTGTTTCATTTTTGTTTTATAATTTCATGTTCTTTCTAGATTTTACATCTTTTTATGCA
TACTAAACATACTCACTTGAAAGTCTTTGTAAGATTGTTCTATAAAATGTTACCTGAAGTGAATTC
```

Fig. 2

```
GGATCCCAATAGGAGTCATTAAAGGCCTGGAAAAGTGGTGCCATTAGGAGAAAAAGAAATGATTT
CTTGAGCTTGCTCTCAGTTCTCTTTTAGGCTGTCTTGTACTCAGCAGAATAGTGAGATCTTCAAAGG
TTGGGGTTTGATAGTGCCTTGAATAATTTTTAACTTTATATTGCCAGCGGAAGAAGCATTCTCTTTT
TAGATTTAAAAAAATGTAGATACAAATATTAGGGGTTTTATTTTTAGTGAAACATTTCAAACATACA
GGAATAGATAATTATGTAATGAACACTCGTATGTCCACCATCTGGCTTTGTAAAATCTTAAAATTAT
GTCTTATGTGCTCAATTGTTTTATTTCATAAAAGATACTGATAAACATAGCTGAAGTCACTTGTATA
CCATTCACCTTCTTCCCTGTAGATTACTATGAACTCGGTCTTTTTATTCTCATACATATTTTTTGTATT
TTTGCAGTATATTTATGTGTTCATAAACAATATGTAATTTTACAATATGTAACACACTAGTAACATA
CTAATTTAAAACTTGTTTTTAGTTTACAATATGTTGTAAACTATTGTAAGCTAAAGACATATTGTAC
AACCTATTGTTAAATAAAAACAGGTTTTAGTTTTAAATTAGGTATGTTACTGGGATCATTCTGCAAC
TTGTTTATTCCTCTCCAGCTTTGATTTGTGGTTTTATTATCTTAACCTACACTTTTAATTAATCCATT
TTATTTGTTACATGGTATTCTATTATATCATAAAAACTTATCTATTCTGTTGGTTTTGTTGTTGGTC
ATTTGAGACCATGTCTTCGCTCTGTCACCCAGGCTGGAGTACAGTGGCGTGATCTTGGCTCACTGTG
ACCTCTGCCTCCCGGATTCAAGTGGTTTTGGTGCCTCAGCCTCCTGAGTAGCTGGGATTATAGGCGT
GTGCCACCATGCCCAGCTAATTTTTGTATTTTTAATAGAGACGGGATTTCACCATGTTGGCCAGGCT
GGTCTTGAACTGACCTCAAGTGATCTGCTCACCTCAGCTGCACAAAGTGCTGGGATTACAGGTGTT
AGCCAACCAATACCCTGCCTCTATTCTCTTGTTAAGAGGCATTTAGCATGGTTAATACAGTCTCTTG
CCCTCATAAACAGTGCTGGGAAGGAAACACATGTTCTTGTGTATATTGAATGAAATTTGTTTATAC
ATTAGATATTTCCAAATGTTCTCTTTAAGTACTTCAGTTTACATCATTACTCTCCTCCTCCCTCCCCT
CCCACCCCCACCCACAACAGTATTCCTCTTTTTCCATATCCTTGCTAATGTTTCAAAGTTTTGCTTTT
TACATTTGGGTCTTAGATCCACTAGAATGTATTTTTGCATTGGGATGAAGTTGAAACCTAATATATT
TTCCAAATGAGTAAACTGTTGTCACAGAACTATTTAGTTGTATTACCTCCTCTCTTGTATATCAGAT
ATATCTACATATATGTCAGACTGTTTCTGGGCTGTCTGTCCTCTTTAATTAGTTCGTGTATCTGTTTC
TGCATCAGTAGCATACTGTCTTAACTACTGTAGCTTTATAAAGTCTATTGAGTAGGACAAGTTGTT
TCATTCTTCAAAATTGCTTGGCTATTCTTGGCCCTCTGCTGTTTCATATTAACTTTCAGATAAACTT
GTCAAATTCTAATGAAAACTGTTGATAAACTTGTTGATTAACAAATTCTAATAAAAACTGTTGAGA
TTTTTATTGGAATTGCAATACATTTATAGATTAACGGAGAAAGATATTGACAATACAATTGAGTTTC
CAATTCACGAACATGTTATACCTCTCCATTAATTCATGTCTTTTGAATGTATCCACCAATATGGTTTT
GTAATTTTCTTCATAAAGGACATTTAAAATTCTTATTTTAAGTGATCTTATAGTTTTATGCTAACGTG
AATGAGATTTTTCCATTATGTTTCTGTTGGTTATTCCTGAAGTGGTAATGCTTATAATTTTGGGGTGT
TGGTCTTGTATCTGCCTAGGCTCGAGTCGAGCTAAAATCGAGCTAAAATCGAGCTAAAATCGAGCT
AAAATCGAGCTAAAATCGAGCTAAAATCGAGCTAAAATCGAGCTAAAATCGAGCTAAAATCGAGC
TAAAATCGAGCTAAAATCGAGCTAAAATCGAGCTAAAATCGAGCTAAAATCGAGCTAAAATCGAG
CTAAAATCGAGCTAAAATCGAGCTAAAATCGAGCTAAAATCGAGCTAAAATCGAGCTAAAATCGA
GCTAAAATCGAGCTCCTAGGAGATACAAGAGGTGCTCAGAGTTGTTCAGGGTTGCTGAACTCTTAG
TTCTAAAAGTGTCTGTCATTTGGGGTTTCTATGTAGATAATTTAATTATCTATAAAAACAGTTCTTC
ATTTTCAGTTCATATATTTCATATTTTCTTAAGTTTTAATTTTTATTTTTAAACACAATTATCCATAA
ACCCTAACCCTTTCCCTAGTCAACAGCAGTCACAGCCAAATGTTTATTAATTGCTATACTCAGTGT
TTCTTGTATCTCATACCTTCTGGGGTTTCTTGTCTTGTTGAAATACACCCTTTAATGTTTCTTAGTG
AAGACCCAACAGTGGCACTCACTCACCTTTGTTTACCTGAAAATTTCTTTATTTTCATCTTAATTCAT
AGTCTGTCTTTTCTCCAGTCAAGGAAGTGTCTTATAGGGAAGATTCTGGTTTCACTATCGTGTATCC
AGGATATATATGTATTTATAGATAGACTTTTAATCTGAGGACTAATGTATTTTATCCTACAGTATTA
CCAATCATTATTTCTTCCATAACTTCTAGACCATTCCTTTTGTACTTCTTTTTTAGAGTCCTTATTAG
ATGAGTGTTGACTCTTTTCAATCTAGACATCTTTTTTAAACTATATTTTCATACTCTTTGTCTCTTTA
GGTCTGATTTTTTAAGTTCAGGGGATATTTCATTTTGGGTGAGTTGTAGCACTACTTCAATTCACTA
ATTCTAATTATATTTAATCTACAAGTTATTCCATCTATAATTTATTTCAATTACCACTTTTTGTTTTCA
AAATTTCTAATTTTATATCTGATTTTGTTTCATTTTTGTTTTATAATTTCATGTTCTTTCTAGATTTTA
CATCTTTTTATGCATACTAAACATACTCACTTGAAAGTCTTTGTAAGATTGTTCTATAAAATGTTAC
CTGAAGTGAATTC
```

POLYNUCLEOTIDES FOR ENHANCING EXPRESSION OF A POLYNUCLEOTIDE OF INTEREST

The present invention relates to polynucleotides comprising a first nucleic acid sequence for a chromatin element, which is capable of enhancing expression, and at least one second nucleic acid sequence comprising a curved origin motif. Furthermore, the invention relates to a host cell, a non-human transgenic organism, a vector and a kit comprising the aforementioned polynucleotide. Moreover, the invention relates to methods for expressing a polynucleotide of interest.

Both in basic research as well as for commercial applications eukaryotic and prokaryotic cells are commonly used for the expression of polynucleotides encoding a product of interest (e.g. a polypeptide or a functional RNA). For the synthesis of a product of interest in a host cell, a gene encoding said product—frequently referred to as the transgene—is introduced into host cells, e.g. by transfection or transformation. The cells are then grown under suitable conditions to express the product of interest. This cultivation step often includes the use of a selectable marker gene which is introduced into the host cells together with the polynucleotide encoding a product of interest in order to select for cells harbouring said polynucleotide. After cultivation, the product, e.g. a recombinant protein, can be purified from the cells by appropriate purification steps.

Generally, both eukaryotic and prokaryotic cells can be used for the expression of recombinant proteins. Prokaryotic expression systems have the advantage of easily producing large amounts of proteins. However, the recombinant proteins produced in such systems are not postranslationally modified and may be included in insoluble inclusion bodies. Eukaryotic expression systems are, preferably, used for proteins which need to undergo extensive posttranslational modifications and/or folding in order to be functional.

For the synthesis of the desired product encoded by the polynucleotide of interest, a strong and a reliably stable expression of the said polynucleotide is of high interest because a strong and stable expression is more cost- and time effective. A strong expression of a polynucleotide is often related to the integration of said polynucleotide into highly transcribed chromatin regions and/or to multiple integration events. Multiple integration events, however, especially in combination with complex so called "inverted repeat" patterns, are more likely to result in transgene silencing, i.e. in an unstable and reduced expression of the polynucleotide.

Within the last decades a lot of effort has been put into enhancing transgene expression in cell systems. E.g., enhanced expression can be achieved by utilizing a strong promoter that drives gene expression. Moreover, the expression of a transgene can be enhanced when the transgene is introduced in the host cell in combination with certain chromatin elements.

Chromatin is a complex consisting of DNA, RNA and proteins inside the nucleus of eukaryotic cells. Generally, chromatin is organized in loops and domains and can exist in different states of condensation. The degree of condensation is thought to affect progresses that require access to DNA like transcription, replication or DNA repair. Generally, a relatively condensed structure is considered to be transcriptionally silent, on the other hand a relatively decondensed ("open") structure is thought to be a prerequisite for efficient gene expression. Presumably, chromatin domains/elements which are capable of enhancing expression of a cotransfected transgene, i.e. a polynucleotide of interest, have binding sites for factors which can decondense the chromatin structure. It is thought that sequence elements in the neighbourhood of these domains are more easily accessible by transcription-related factors, thus showing a higher expression.

WO 02/24930 discloses ubiquitous chromatin opening elements (UCOEs) which are capable of enhancing transgene expression in mammalian cells.

Zahn-Zabal et al. (J Biotechnol., 2001, 87(1):29-42) discloses a chicken lysozyme matrix attachment region (MAR) that significantly increases stable expression of a co-transfected reporter gene resulting in an increased proportion of high-producing clones.

WO2005/040377 discloses DNA sequences having protein production increasing activity and the use of these DNA sequences in order to increase protein production activity in a eukaryotic cell.

Kalos and Fournier (Mol Cell Biol., 1995, 15(1):198-207) discloses that elements of the apolipoprotein B (apoB) chromatin domain which is flanked by Matrix attachment regions mediate transgene expression.

Klehr et al. (Biochemistry, 1991, 30(5):1264-70) suggests that human scaffold-attached regions from the human interferon beta domain can be used to enhance the expression of genes. Moreover, it was shown that scaffold attachment regions (SARs) enhance general promoter functions in an orientation- and partially distance-independent manner.

Dang et al (J Virol., 2000, 74(6):2671-8) discloses that the insertion of a 2 kb fragment of the human beta interferon scaffold attachment region (IFN-SAR) causes a stable expression of the genes on this vector.

EP 1 676 916 discloses a non-coding 12 kb nucleic acid sequence of the 5' region and a 4 kb nucleic acid sequence of the 3' region of the elongation factor 1 $\alpha$ for enhancing the expression of a cotransfected transgene.

To increase productivity, gene amplification cell engineering techniques can be applied in which the amplifiable gene is used as a selectable marker for the transfected vector. In a first step, the vector which contains the transgene and the amplifiable marker gene is introduced into the host cell. When the selectable and amplifiable gene is amplified, genetically linked sequences containing the transgene are co-amplified. Amplification is induced by a time-consuming multistep selection process increasing stepwise the concentration of the selective agent. Subsequent screening of subcloned resistant cells can lead to identification of highly productive cell lines. Amplifiable and selectable markers for gene amplification in mammalian cells are reviewed by T. Omasha in Journal of Bioscience and Bioengineering (2002) 94, 600-605.

Furthermore, the expression of a transgene can be increased by using a modified selectable marker having a reducing activity for the selection of transfected cells. WO/2004/050884 discloses an expression system that enhances the proportion of high producers in a cell population. The use of a modified neomycin phosphotransferase as a marker for the selection of transfected CHO cells enhanced the ratio of high-producing cells to total cell number.

Although, the level of expression of a polynucleotide of interest in host cells can be increased by the described techniques, high expression frequently results in silencing of the expression, i.e. in a reduced and unstable expression. Due to gene silencing effects, cell clones which strongly express a polynucleotide of interest at the beginning of cultivation may show a significantly reduced expression during the course of cultivation. Moreover, if the proportion of unstably expressing cells in a cell population is very high, single high-producing clones may have to be isolated by time- and cost-intensive screening procedures in order to get sufficient amounts of the desired product.

Thus, an expression system which allows for an improved expression of a polynucleotide of interest, i.e. a strong and stable expression, without the drawbacks as referred to above is highly desired.

Thus, the technical problem underlying the present invention may be seen as the provision of means and methods for improving gene expression in host cells whereby a high (efficient) and reliably stable expression is achieved.

Accordingly, the present invention relates to a polynucleotide comprising a first nucleic acid sequence for a chromatin element, which is capable of enhancing expression, and at least one second nucleic acid sequence comprising a curved origin motif. Preferably, such a polynucleotide allows for enhanced expression of a polynucleotide of interest that is introduced into a host cell in combination with said polynucleotide.

The term "polynucleotide" as used herein relates to a nucleic acid sequence. The nucleic acid sequence may be a DNA or a RNA sequence, preferably the nucleic acid sequence is a DNA sequence.

The polynucleotides of the present invention either essentially consist of the aforementioned nucleic acid sequences or comprise the aforementioned nucleic acid sequences. Thus, they may contain further nucleic acid sequences as well.

The polynucleotides of the present invention shall be provided, preferably, either as an isolated polynucleotide (i.e. isolated from its natural context) or in genetically modified form. An isolated polynucleotide as referred to herein also encompasses polynucleotides which are present in cellular context other than their natural cellular context, i.e. heterologous polynucleotides. The term polynucleotides encompasses single as well as double stranded polynucleotides. Moreover, comprised are also chemically modified polynucleotides including naturally occurring modified polynucleotides such as glycosylated or methylated polynucleotides or artificial modified one such as biotinylated polynucleotides.

The term "expression" as used herein refers to transcription only or transcription and translation, occurring within a host cell. It is to be understood that the term expression, preferably, relates to transcription or transcription and translation of at least one polynucleotide of interest that was cointroduced into a host cell together with at least one polynucleotide of the present invention. The term "cointroduced" as used herein means that the introduction of various polynucleotides into a host cell, e.g. by transfection or transformation techniques, preferably, is carried out at the same time, i.e. simultaneously. Thereby, preferably an integration of cointroduced sequences in nearby chromatin regions shall be possible.

The term "polynucleotide of interest" as used herein relates to a nucleic acid sequence. The nucleic acid sequence may be a RNA or DNA sequence, preferably, the nucleic acid sequence is a DNA sequence. In accordance with the methods of the present invention the polynucleotide of interest may encode for product of interest. A product of interest may be a polypeptide of interest, e.g. a protein, or a RNA of interest, e.g. a functional RNA, e.g. a double stranded RNA, microRNA, or siRNA. Functional RNAs are frequently used to silence a corresponding target gene. Preferably, the polynucleotide of interest is operatively liked to suitable regulatory sequences (e.g. a promoter) which are well known and well described in the art and which may effect the transcription of the polynucleotide of interest.

The level of expression of a desired product in a host cell may be determined on the basis of either the amount of corresponding mRNA that is present in the cell, or the amount of the desired product encoded by polynucleotide of interest. For example, mRNA transcribed from a selected sequence can be quantitated by PCR or by Northern hybridization (see Sambrook et al., Molecular Cloning: A Laboratory Manual, Cold Spring Harbor Laboratory Press (1989)). Polypeptides can be quantified by various methods, e.g. by assaying for the biological activity of the polypeptides (e.g. by enzyme assays), or by employing assays that are independent of such activity, such as western blotting, ELISA, or radioimmunoassay, using antibodies that recognize and bind to the protein.

The term "nucleic acid sequence for a chromatin element which is capable of enhancing expression" as used herein relates to a nucleic acid sequence for a chromatin element or domain which can enhance the expression of a polynucleotide. Preferably, the term relates to a nucleic acid sequence for a chromatin element which is capable of enhancing the expression of a polynucleotide of interest that was cointroduced into a host cell with said chromatin element. Chromatin elements/domains which are capable of enhancing expression of a polynucleotide of interest (e.g. MARs or ubiquitous chromatin opening elements) are well known in the art and described, e.g. in EP 1 676 916, WO2005/040377, WO 0224930, Dang et al., Klehr et al., Kalos et al., Zahn-Zabal et al. (all loc. cit.). Moreover, non random genomic dispersed genetic elements which can regulate gene activity by influencing the architecture of chromatin are described by Hodgetts in Current Opinion in Genetics & Development (2004) 14 680-685. WO2005/040377 describes, e.g., DNA sequences having protein production increasing activity and the use of these DNA sequences in order to increase protein production activity in a eukaryotic cell. Preferably, a chromatin element which is capable of enhancing expression is a nucleic acid element whose integration into chromatin (i.e. into the chromosomal DNA) may cause a more decondensed ("open") chromatin structure, preferably a more decondensed structure of chromatin regions flanking the integration site.

As set forth above, a preferred chromatin element comprises a DNA element having matrix attaching activity. It is to be understood that said DNA element is capable of enhancing expression of a cotransfected polynucleotide of interest. Preferably, the chromatin element comprises a MAR which is capable of enhancing expression. Matrix attachment regions are specific DNA sequences located at the bases of chromatin loops that anchor the DNA to the fibers of the nuclear matrix. Matrix attachment regions are similar to SARs (Scaffold attachment regions) and hence are also referred to as SARs or Scaffold/matrix attachment regions (S/MARs). It is known, that MAR containing sequences can repress promoter activity (Lauber et al. J Biol Chem. 1997 Sep. 26; 272(39):24657-65.). Also the presence of specific MAR elements does not result in less position-induced variation in the average level of transgene expression (Van Leeuwen et al. Plant Mol Biol. 2001 November; 47(4):543-54). Interestingly a MAR sequence of the mouse perforin gene exerted a global silencing effect (Mol Cells. 2002 Feb. 28; 13(1):61-8.). Also MAR-beta, a matrix-associated region located upstream of the T cell receptor beta enhancer, serves a crucial role in silencing Ebeta-mediated TCR activation (Kaul-Ghanekar et al. Nucleic Acids Res. 2004 Sep. 15; 32(16):4862-75). Specific MAR sequences are known to be capable of enhancing expression of genes, e.g. of cointroduced transgenes, and may function as origin of replication Although no clear consensus sequence can be defined for an entire MAR, several DNA sequence motifs are typically found in MARs like origins of replication, TG-rich sequences, curved DNA motifs, kinked DNA motifs, Topoisomerase sites, AT rich sequences. These motifs are well known in the art and, e.g., are listed in Singh et al. (Nucleic Acids Research, 1997, 25(7): 1419-1425), which is herewith incorporated by reference in respect to the disclosed polynucleotide sequences and in its entirety. Furthermore, S/MAR prediction programs allow for predicting MARs or SARs from genomic sequences (e.g. Fiorini et al., Biochemistry (Moscow), 2006, 71(5): 481-488).

The chromatin element referred to herein, being capable of enhancing expression, preferably, comprises the nucleic acid sequence as shown in SEQ ID NO:28 (amplified from genomic DNA from human leukozytes, see Example 1). More preferably, the chromatin element comprises the nucleic acid sequence as shown in SEQ ID NO:27 (amplified from genomic DNA from HeLa cells) comprising the AT rich MII region of intron 13 of human topoisomerase I (GenBank L23999.1; GI: 398042; Romig et al., 1994, Eur J Biochem. 221:411-419).

The MAR element of the chicken lysozyme 5' matrix attachment region is also known to be capable of increasing the expression of a transgene (Girod et al. Biotechnol Bioeng. 2005 Jul. 5; 91(1):1-11)

Enhancing expression as used herein means improving or increasing expression including transcription, or transcription and translation of a polynucleotide encoding a product of interest whereby said polynucleotide has been cointroduced into a host cell with a polynucleotide of the present invention. Preferably, the amount of the product of interest is increased. This can be either due to a more stable expression or due to a stronger expression, or both. Enhanced expression can be shown by comparing the expression of the polynucleotide of interest having been co-introduced into the host cell together with a polynucleotide according to the invention with the expression in a reference host cell. Preferably, the reference host cell is a host cell generated by introducing the same polynucleotide of interest without the additional introduction of a polynucleotide according to the invention. Means and methods for determining the amounts of polypeptides (e.g. by western blotting, by Elisa or by enzyme assays, supra) and RNA molecules (e.g. by PCR or Northern blotting, supra) and for comparing said amounts are well known in the art. Preferably, the amount of the desired product is statistically significant increased compared to the reference amount, more preferably, the amount of the desired product is increased twofold, threefold, fourfold, fivefold, tenfold, twenty fold, thirty fold, fifty fold, one hundredfold, two hundredfold or one thousand fold.

The term "curved origin motif" as used herein is to be understood as a combination of at least one origin of replication signal (also referred to as "replication origin signal", "origin signal", or "ori signal") and at least one curved DNA signal. Preferably, the curved origin motif comprises one, two, three, four, five, seven, ten, fifteen, twenty, twenty-one, twenty-five, thirty, thirty-five, forty, fifty, fifty-five, sixty, seventy, eighty, ninety, one hundred, two hundred, five hundred, one thousand, or more origin of replication signals and one, two, three, four, five, seven, ten, fifteen, twenty, twenty-one, twenty-five, thirty, thirty-five, forty, fifty, fifty-five, sixty, seventy, eighty, ninety, one hundred two hundred, five hundred, one thousand, or more curved DNA signals. A curved origin motif according to the invention may comprise different ori signals. Moreover, curved origin motif according to the invention may comprise different curved DNA signals. Singh et al. (Nucleic Acids Research, 1997, 25(7), 1419-1425) which is hereby incorporated by reference in its entirety, discloses ori signals as well as curved DNA signals. Curved DNA signals as meant herein are nucleic acid sequences characterized in that these sequences are capable of introducing (intrinsic) curvature into a DNA molecule containing them. The person skilled in the art knows nucleic sequence elements which introduce curvature into a DNA molecule. For example, curvature may occur when short homopolymeric runs (4 to 6 bp) of, e.g., adenines ("A tracks") are repeated in phase with the helical screw. One helical screw comprises approximately 10.4 bp (see Haran et al., 1994, Sequence elements responsible for DNA curvature. J Mol Biol, 244: 135-143). Curvature of a DNA fragment may be determined, e.g., by the electrophoretic mobility of the DNA fragment or may be predicted by using a suitable computer software (e.g. as described in Shpigelman et al, 1993, Comput Appl Biosci.; 9(4):435-40). Curved DNA, for example, has been identified at or in proximity several matrix attachment sites. Curved DNA may play an important role in nuclear processes that involve the interaction of DNA and proteins, such as recombination, replication, and transcription. Curvature into DNA sequence elements may be introduced by DNA motifs, comprising curved DNA signals having the nucleic acid sequence of AAAANNNNNNNAAANNNNNNAAAA (as shown in SEQ ID NO:18), or AAAANNNNNNAAAANNNNNNAAAA (as shown in SEQ ID NO:19), or TTTTNNNNNNNTTT-NNNNNNNTTTT (as shown in SEQ ID NO:20), or TTTT-NNNNNNNTTTTNNNNNNNTTTT (as shown in SEQ ID NO:21), wherein N represents any nucleotide, thus A, T, C or G or a chemically modified derivative of any of the said nucleotide, preferably N represents G or C. Particularly, curvature is introduced by repeats/multimers of these signals.

Moreover, curvature into DNA sequence elements may be introduced by DNA motifs, comprising curved DNA signals, preferably multimers/repeats of curved DNA signals, more preferably multimers/repeats of curved DNA signals which are approximately in phase with the helical screw, the curved DNA signals having the nucleic acid sequence of AAAANNNNN (as shown in SEQ ID NO:37), or AAAANNNNNN (as shown in SEQ ID NO:38), or AAAAANNNNN (as shown in SEQ ID NO:39), or AAAAANNNNNN (as shown in SEQ ID NO:40), AAAAAANNNNN (as shown in SEQ ID NO:41), or AAAAAANNNNNN (as shown in SEQ ID NO:42), or TTTT-NNNNN (as shown in SEQ ID NO:43), or TTTT-NNNNNN as shown in SEQ ID NO:44), or TTTT-NNNNNN (as shown in SEQ ID NO:45), or TTTTTNNNNNN (as shown in SEQ ID NO:46), or TTTTTTNNNN (as shown in SEQ ID NO:47), or TTTTTT-NNNNN (as shown in SEQ ID NO:48), wherein N represents any nucleotide, thus A, T, C or G or a chemically modified derivative of any of the said nucleotide, preferably N represents a G or C. Moreover, curvature into DNA sequences is introduced by the curved DNA signals TTTAAA (as shown in SEQ ID NO:22), and AAATTT (as shown in SEQ ID NO:23), (e.g. in Singh et al., supra), especially by multimers/repeats of these signal.

An ori signal is an element of an ori, preferably AT rich. The person skilled in the art knows oris (origins of replication). An ori is a DNA sequence at which DNA replication can be initiated. The DNA sequence of an ori can vary from species to species, particularly from prokaryotes to eukaryotes, however ori motifs generally share some common properties. Ori signals as used herein are, preferably, sequence motifs derived from eukaryotic replication origins, however also may be signals/motifs derived from prokaryotic replication origins. Eukaryotic oris are well described, for instance, for the budding yeast *Saccharomyces cerevisiae*, for which specific sequences conferring origin activity (called Autonomously Replicating Sequences or ARS elements) have been isolated. It is known that DNA replication is associated with the nuclear matrix. It has also been demonstrated that nuclear matrix attachment sites, homeotic protein recognition and binding sites and origins of replication share the following ori signals: ATTA (as shown in SEQ ID NO:24), ATTTA (as shown in SEQ ID NO:25), and ATTTTA (as shown in SEQ ID NO:26), (e.g. in Singh et al., loc. cit.).

The curved DNA signal(s) and ori signal(s) of a curved origin motif may be spaced, i.e. separated by additional nucleic acid sequences. Moreover, the nucleic acid sequences of a curved DNA signal and an ori signal may overlap, i.e. a nucleotide which is an element/part of an ori signal, may also be an element of a curved DNA signal. Moreover, a curved DNA signal may comprise one or more ori signals, and vice versa. Examples for an overlap of curved DNA and ori signals are, e.g., the curved origin motifs as shown in SEQ ID NO:1, SEQ ID NO: 2, SEQ ID NO:29, or SEQ ID NO:31 (see below). It is to be understood that a curved origin motif in accordance with the present invention is capable of introducing curvature into the DNA containing it. Curvature can be determined by means and methods as described above. Moreover, it is to be understood that a curved origin motif may also comprise combinations of various curved origin motifs.

In a preferred embodiment of the invention, the curved origin motif comprises the nucleic acid sequence ATTTTANNNNNATTTTANNNNNATTTTA as shown in SEQ ID NO:1, or at least two repeats of the nucleic acid sequence ATTTTANNNNNATTTTANNNNNATTTTANNNNN as shown in SEQ ID NO:29 (and thus at least twice the nucleic acid as shown in SEQ ID NO:29 resulting in at least a dimer of said nucleic acid sequence), the nucleic acid sequence TAAAATNNNNNTAAAATNNNNNTAAAAT as shown in SEQ ID NO:2, or at least two repeats of the nucleic acid sequence TAAAATNNNNNTAAAATNNNNNTAAAATNNNNN as shown in SEQ ID NO:30, whereby N stands for any nucleotide, i.e. A, T, C or G, preferably a for C or G, or a chemically modified derivative of any of the said nucleotides. More preferably, the curved origin motif comprises the nucleic acid sequence ATTTTAGCTCGATTTTAGCTCGATTTTA as shown in SEQ ID NO:31, or at least two repeats of the nucleic acid sequence ATTTTAGCTCGATTTTAGCTCGATTTTAGCTCG as shown in SEQ ID NO:32, or the nucleic acid sequence TAAAATCGAGCTAAAATCGAGCTAAAAT as shown in SEQ ID NO:33, TAAAATCGAGCTAAAATCGAGCTAAAATCGAGC as shown in SEQ ID NO:34, or at least two repeats of the nucleic acid sequence AAAATCGAGCTAAAATCGAGCTAAAATCGAGCT as shown in SEQ ID NO:75. The term "at least two repeats" as used herein, preferably, means two or more than two repeats (and thus two or more than two units or monomers), preferably, at least three, at least four, at least five, at least six, at least seven or at least ten, at least twenty, at least thirty, at least forty, at least fifty, at least one hundred, at least two hundred repeats/units/monomers. Accordingly, the curved origin motif, preferably, comprises twice or more than twice, or more than three times etc. the respective nucleic acid as referred to herein above and, thus, preferably is a dimer (when comprising two repeats), trimer (when comprising three repeats), oligomer, multimer etc. of the aforementioned nucleic acids. A particularly preferred number of curved origin motifs to be included into the chromatin element of the present invention is seven. Another particularly preferred number of curved origin motifs to be included into the chromatin element of the present invention is twenty-two. Preferably, said at least two repeats are direct repeats (head to tail repeats, preferably, without any additional nucleotides between the repeats).

Moreover, the curved origin motif may comprise at least one repeat of the nucleic acid sequence (and, thus, at least once the nucleic acid sequence) TAAAATNNNN (as shown in SEQ ID NO:49), or TAAAATNNNNN (as shown in SEQ ID NO:50), or TAAAAATNNN (as shown in SEQ ID NO:51), or TAAAAATNNNN (as shown in SEQ ID NO:52), TAAAAAATNN (as shown in SEQ ID NO:53), or TAAAAAATNNN (as shown in SEQ ID NO:54), or ATTTTANNNN (as shown in SEQ ID NO:55), or ATTTTANNNNN (as shown in SEQ ID NO:56), or ATTTTTANNN (as shown in SEQ ID NO:57), or ATTTTTANNNN (as shown in SEQ ID NO:58), or ATTTTTTANN (as shown in SEQ ID NO:59), or ATTTTTTANNN (as shown in SEQ ID NO:60), wherein N represents any nucleotide, thus A, T, C or G or a chemically modified derivative of any of the said nucleotide, preferably N represents a G or C. The term "at least one repeat" as used herein means one or more than one repeat/unit/monomer, preferably, at least two, at least three, at least four, at least five, at least six, at least seven or at least ten, at least twenty, at least twenty-two at least thirty, at least forty, at least fifty, at least seventy-five at least one hundred, at least two hundred repeats/units/monomers. As laid out above, a particularly preferred number of curved origin motifs to be included into the chromatin element of the present invention is twenty-two. Preferably, said repeats are direct repeats (see above).

In another more preferred embodiment of the invention the curved origin motif comprises the nucleic acid sequence as shown in SEQ ID NO:7 or SEQ ID NO:8, or SEQ ID NO:9, or SEQ ID NO:10.

In accordance with the present invention, the nucleic acid sequence for the curved origin motif is covalently linked to the nucleic acid sequence for the chromatin element. The person skilled in the art knows techniques that can be used for covalently linking two or more nucleic acid sequences, e.g. techniques known as recombinant DNA techniques such as ligation or cloning. It is to be understood that the curved origin motif is additionally integrated into a chromatin element which is capable of enhancing expression. Thereby, a "synthetic" chromatin element is generated. It is to be understood that the nucleic acid sequence for the curved origin motif may be in any position of the nucleic acid sequence for the chromatin element. Preferably, the curved origin motif is introduced at a position between nucleotide 1900 and 2200, more preferably, between 2000 and 2100, and most preferably, at position 2031 of SEQ ID NO:27.

Moreover, it is to be understood that the chromatin element which is capable of enhancing expression of a cotransfected polynucleotide may comprise a nucleic acid sequence for a curved origin motif in more than one position, e.g. in two, three, four, five, ten, twenty, thirty, forty, fifty or in one hundred positions, preferably, said polynucleotide comprises said nucleic acid sequence in one position.

In another most preferred embodiment of the invention, the polynucleotide comprising a first nucleic acid sequence for a chromatin element, which is capable of enhancing expression, and at least one second nucleic acid sequence comprising a curved origin motif has a nucleic acid sequence as shown in SEQ ID NO:3 or in SEQ ID NO:4 or SEQ ID NO:5 or in SEQ ID NO:6 or a variant of any one of the said SEQ ID Nos. Such variants, preferably, have a nucleic acid sequence being at least 70%, at least 80%, at least 90%, at least 95%, at least 96%, at least 97%, at least 98% or at least 99% identical to any one of SEQ ID NOs: 3, 4, 5 or 6. The degree of identity (percentage, %) between two or more nucleic acid sequences is, preferably, determined by the algorithms of Needleman and Wunsch or Smith and Waterman. To carry out the sequence alignments, the program PileUp (J. Mol. Evolution., 25, 351-360, 1987, Higgins 1989, CABIOS, 5: 151-153) or the programs Gap and BestFit (Needleman 1970, J. Mol. Biol. 48; 443-453 and Smith 1981, Adv. Appl. Math. 2; 482-489), which are part of the GCG software packet (Genetics Computer Group, 575 Science Drive, Madison, Wis., USA 53711, vers. 1991), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. Moreover, the said variant nucleic acid sequence, preferably, comprises at least one curved origin motif as specified above. Preferably, a polynucleotide comprising such a variant nucleic acid sequence is capable of enhancing expression of a cotransfected polynucleotide. This enhancement can be tested by the assays described in the accompanying Examples.

The present invention also relates to curved origin motifs as specified above. Preferably, said motifs are used for enhancing expression of a cotransfected transgene.

Advantageously, it has been found in accordance with the present invention that the cointroduction of a polynucleotide comprising a first nucleic acid sequence for a chromatin element, which is capable of enhancing expression, and at least one second nucleic acid sequence comprising a curved origin motif and of a polynucleotide of interest into a host cell enhances the expression of the polynucleotide of interest. For example, a polynucleotide comprising the AT rich region of the MII region of Intron 13 of the human topoisomerase I (Romig, 1994 Eur J Biochem. 221:411-419) and a curved origin motif was simultaneously transfected together with the pEGFP-N1 vector from Clontech harbouring the reporter gene EGFP (Enhanced Green Fluorescent Protein) and an unmodified neomycin phosphotransferase gene as a selectable marker into CHO cells (Chinese Hamster Ovary). As controls, the pEGFP-N1 vector alone, or the pEGFP-N1 vector in combination with DNA for the AT rich region of the MII region of Intron 13 of the human topoisomerase I without a curved origin motif, were introduced into CHO cells. After transfection cells were selected by cultivation in G418 containing medium (0.6 mg/ml G418). After 10 days single G418 resistant clones formed colonies. Whole resistant cell populations were used for quantification of reporter gene expression by FACS analysis (Fluorescent Activated Cell Sorting). It has been found that compared to the controls the proportion of high expressing cells and, thus, the expression was significantly increased in CHO cells that were generated by cointroducing the reporter gene and said AT rich region comprising a curved origin motif into CHO cells. Thus, the insertion of a curved origin motif into a chromatin element, which per se is capable of enhancing expression of a cotransfected polynucleotide of interest, further enhances the expression enhancing effect of said chromatin element. When only a curved motif (instead of a curved origin motif) was integrated in said chromatin element, compared with said chromatin element alone (without inserted curved motif) surprisingly no enhancement of expression was detectable. The surprising expression enhancing effect was shown, e.g. for polynucleotides having a nucleic acid sequence as shown in SEQ ID NO:3, SEQ ID NO:4 and SEQ ID NO:5. Thus, the use of the aforementioned polynucleotide according to the invention will reduce the time- and cost-intensive screening steps for isolating high producing clones.

Moreover, the invention relates to a polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16.

Said polynucleotides encode for a modified neomycin phosphotransferase II (NPT II) having 1 or 2 amino acid changes in the amino acid sequence as compared to the unmodified ("wild-type") neomycin phosphotransferase having an amino acid sequence as shown in SEQ ID NO:35. Specifically, it is envisaged that a modified NPT II of the present invention shall have an amino acid substitution of R to A and R to V, respectively, at a position corresponding to position 226 of the NPTII as described in SEQ ID NO:11 and SEQ ID NO:12, respectively, or of A to G and T to S at a position corresponding to position and 224 and 225, respectively, of the NPTII as described in SEQ ID NO:13. The NPTII gene, also referred to as the neomycin-resistance gene was initially isolated from the Transposon Tn5 of the *E. coli* strain K12. The NPT II protein belongs to a class of enzymes that inactivate aminoglycoside-aminocyclitol antibiotics by regiospecific phosphorylation. It confers resistance to various aminoglycoside antibiotics, such as kanamycin and G418. The gene is commonly used as a selectable marker for the transformation of a large variety of organisms like bacteria, plants, animals and yeast. It is known in the art that modifications, i.e. amino acid changes, in the NPT II amino acid sequence may reduce the enzymatic activity of NPT II. Moreover, it is known that the use of mutated NPT II variants having a reduced enzymatic activity for transformation may result in transgenic organisms that are less resistant against neomycin than organisms harbouring the unmodified NPT II gene. Moreover, these variants can be used for the selection of high-producing cells (see e.g. WO 2004/050884).

It is to be understood that the polynucleotides of the present invention encoding for a modified neomycin phosphotransferase may encode fusion proteins wherein one partner of the fusion protein is a polypeptide being encoded by a nucleic acid sequence recited above. Such fusion proteins may comprise as additional part other enzymes of the fatty acid or lipid biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

Moreover, the present invention relates to polypeptides encoded by a polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16.

Advantageously, in accordance with the present invention it has been shown that the use of a polynucleotide comprising a nucleic acid sequence as shown in any one of SEQ ID NO:14, SEQ ID NO:15 and SEQ ID NO:16 as a selectable marker gene for the transfection of CHO cells, particularly, enhances the expression of a cointroduced polynucleotide of interest. For example, various vectors comprising modified NPT II genes and the reporter gene EGPF were introduced into CHO cells. After transfection, cells were selected by cultivating said cells in G418 containing medium (0.6 mg/ml). Comparative experiments were carried out in which instead of a modified NPT II a polynucleotide encoding an unmodified neomycin phosphotransferase was used as a selectable marker. It has been found that the proportion of high expressing cells, thus the reporter gene expression, was significantly enhanced in transgenic host cells generated by using a modified neomycin phosphotransferase as a selectable marker. Thus, the use of the mentioned polynucleotide according to the invention will reduce the time- and cost-intensive screening steps for isolating high producing clones.

The present invention also relates to a host cell comprising a polynucleotide as specified above comprising a first nucleic acid sequence for a chromatin element, which is capable of enhancing expression, and at least one second nucleic acid sequence comprising a curved origin motif, or a polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16, or a combination thereof.

As used herein, a "host cell" includes any cultivatable cell that can be modified by the introduction of heterologous DNA. Preferably, a host cell is cell in which a polynucleotide of interest can be stably expressed and a polypeptide encoded by said polynucleotide can be post-translationally modified, localized to the appropriate subcellular compartment. The choice of an appropriate host cell will also be influenced by the choice of detection signal. A host cell of the present invention includes prokaryotic cells and eukaryotic cells. Prokaryotes include gram negative or gram positive organisms, for example, *E. coli* or *Bacilli*. It is to be understood that prokaryotic cells will be used, preferably, for the propagation of the polynucleotides according to the invention, particularly a vector (see below) comprising polynucleotides of the present invention. Suitable prokaryotic host cells for transformation include, for example, *E. coli*, *Bacillus subtilis*, *Salmonella typhimurium*, and various other species within the genera *Pseudomonas*, *Streptomyces*, and *Staphylococcus*. Eukaryotic cells include, but are not limited to, animal cells, vertebrate cells, yeast cells, plant cells, fungal cells, insect cells (e.g., SF9 cells which could be infected by baculovirus), mammalian cells, reptile cells, algae cells and the cells of parasitic organisms, e.g., trypanosomes. As used herein, yeast includes not only yeast in a strict taxonomic sense, i.e., unicellular organisms, but also yeast-like multicellular fungi of filamentous fungi. Exemplary species include *Kluyverei lactis*, *Schizosaccharomyces pombe*, and *Ustilaqo maydis*, with *Saccharomyces cerevisiae* being preferred. Other yeasts which can be used in practicing the present invention are *Neurospora crassa*, *Aspergillus niger*, *Aspergillus nidulans*, *Pichia pastoris*, *Candida tropicalis*, and *Hansenula polymorpha*. Mammalian host cell culture systems include established cell lines such as COS cells, L cells, 3T3 cells, HeLa cells, baby hamster kidney (BHK) cells, Chinese hamster ovary (CHO) cells, embryonic stem cells.

In a preferred embodiment of the invention the host cell is a mammalian cell. In a more preferred embodiment the host cell is a CHO cell. CHO cell culture systems include all CHO cells which can be cultivated in serum-containing or/and serum-free medium such as CHO-K1, CHO-S, CHO DG44, CHO DXB11, CHO (protein free) ECACC No. 00102307, CHO/dhfr-AC-free ECACC No. 05011002 cells.

Moreover, the present invention relates to a non-human transgenic organism comprising a polynucleotide as specified above comprising a first nucleic acid sequence for a chromatin element, which is capable of enhancing expression, and at least one second nucleic acid sequence comprising a curved origin motif, or a polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16, or a combination thereof.

In accordance with the present invention a non-human transgenic organism may be a non-human animal or a plant. A transgenic non-human animal as meant herein shall have cells that contain a transgene, wherein the transgene was introduced into the non-human animal or an ancestor of the said non-human animal at a prenatal, e.g., an embryonic, stage. A transgene is a DNA which is integrated into the genome of a cell from which a transgenic non-human animal develops and which remains in the genome of the mature non-human animal, thereby directing the expression of an encoded gene product in one or more cell types or tissues of the transgenic non-human animal. Preferred non-human transgenic animals are selected from the group consisting of mouse, goat, sheep, pig, cow, horse, fish, and non-human primates. Non-human farm animals are useful for large scale production of proteins (so called "gene farming"). A transgenic non-human animal can be created, for example, by introducing a transgene into the male pronuclei of a fertilized oocyte, e.g., by microinjection, and allowing the oocyte to develop in a pseudopregnant female foster animal. Methods for generating transgenic animals, particularly animals such as mice, have become conventional in the art and are described, for example, in U.S. Pat. Nos. 4,736,866 and 4,870,009 and Hogan 1986, A Laboratory Manual, Cold Spring Harbor, N.Y., Cold Spring Harbor Laboratory. A transgenic founder animal can be used to breed additional animals carrying the transgene. Transgenic animals carrying a transgene according to the present invention can further be bred to other transgenic animals carrying other transgenes, e.g., to a transgenic animal which expresses a polynucleotide encoding a tetracycline-dependent transcriptional regulator (discussed in more detail herein below). The invention also provides a homologous recombinant non-human animal comprising the vector or expression control sequence of the present invention, preferably in form of a transgene, as referred to above. In such a non-human homologous recombinant animal, said nucleic acids have been introduced into a specific site of the genome, i.e., the nucleic acid molecule has homologously recombined with an endogenous gene or other part of the genome. In said case, the animal, preferably, is a mouse. To create such a homologous recombinant animal, preferably, a vector is prepared which contains DNA encoding the nucleic acid to be introduced flanked at its 5' and 3' ends by additional nucleic acids of a gene or part of the genome at which homologous recombination shall occur. The additional nucleic acid flanking that encoding the fusion protein is of sufficient length for successful homologous recombination with the eukaryotic gene. Typically, several kilobases of flanking DNA (both at the 5' and 3' ends) are included in the vector (see e.g., Thomas, 1987, Cell 51:503 for a description of homologous recombination vectors). The vector is introduced into an embryonic stem cell line (e.g., by electroporation) and cells in which the introduced DNA has homologously recombined with the endogenous DNA are selected (see e.g., Li 1992, Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA. These "germline transmission" animals can further be mated to animals carrying a gene encoding a tetracycline dependent transcriptional regulator. In addition to the homologous recombination approaches described above, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis 1993, Nucl. Acids Res. 21:2025-2029; and Fukushige 1992, Proc. Natl. Acad. Sci. USA 89:7905-7909) and the FLP recombinase-FRT target system (e.g., as described in Dang 1992, Dev. Genet. 13:367-375; and Fiering 1993, Proc. Natl. Acad. Sci. USA 90:8469-8473).

The term "plant" as used herein encompasses plants and algae. Preferably, the term relates to multicellular land plants. More preferably, the multicellular land plants are higher plants such as crop plants including maize, canola, soybean, rice, tagetes, brassica, tricium, or glycine. In principle, transgenic plants can be obtained as described in Becker 1992, Plant Mol. Biol. 20:1195-1197, Bevan 1984, Nucleic Acids Res. 12:8711-8721, and "Vectors for Gene Transfer in Higher Plants" in: Transgenic Plants, Vol. 1, Engineering and Utilization, eds.: Kung and R. Wu, Academic Press, 1993, p. 15-38. Preferably, transformation of plant cells and, thus, generation of transgenic plants, will be achieved by *Agrobacterium*-mediated transformation or by applying physical forces (e.g. "gene gun").

The present invention also relates to a vector comprising a polynucleotide as specified above comprising a first nucleic acid sequence for a chromatin element, which is capable of enhancing expression, and at least one second nucleic acid sequence comprising a curved origin motif, or a polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16, or a combination thereof.

The term "vector", preferably, encompasses phage, plasmid, viral or retroviral vectors as well artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells.

More preferably, in the vector of the invention the polynucleotides according to the invention are operatively linked to expression control sequences allowing expression or propagation in prokaryotic or eukaryotic cells, particularly in eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogene) or pSPORT1 (GIBCO BRL). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

The present invention also relates to a kit comprising a polynucleotide as specified above comprising a first nucleic acid sequence for a chromatin element, which is capable of enhancing expression, and at least one second nucleic acid sequence comprising a curved origin motif, or a polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16, or a combination thereof.

The polynucleotides of the present invention may be provided together with other components required for expression of nucleic acids of host cells in a host cell as a kit adopted for carrying out the method of the present invention. Other components of a kit are, preferably, a host cell to be used for expression or/and substances to be used for the introduction of the polynucleotides into the cell.

The term "kit" as used herein refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention is to be used for practising the methods referred to herein above. It is, preferably, envisaged that all components are provided in a ready-to-use manner for practising the methods referred to above. Further, the kit preferably contains instructions for carrying out the said methods. The instructions can be provided by a users manual in paper- or electronic form.

For example, the manual may comprise instructions for interpreting the results obtained when carrying out the aforementioned methods using the kit of the present invention.

The definitions and explanations of the terms made above apply mutatis mutandis for the following embodiments.

The present invention also relates to a method for expressing at least one polynucleotide of interest, comprising
(a) introducing into host cells
(i) a polynucleotide comprising a first nucleic acid sequence for a chromatin element, which is capable of enhancing expression, and at least one second nucleic acid sequence comprising a curved origin motif, and
(ii) at least one polynucleotide of interest, and
(b) cultivating said host cells.

In the method according to the invention a polynucleotide comprising a first nucleic acid sequence for a chromatin element, which is capable of enhancing expression, and at least one second nucleic acid sequence comprising a curved origin motif is used for the expression of at least one polynucleotide of interest. Preferably, a polynucleotide comprising a first nucleic acid sequence for a chromatin element, which is capable of enhancing expression, and at least one second nucleic acid sequence comprising a curved origin motif is used for enhancing the expression of at least one polynucleotide of interest. The term "at least one polynucleotide of interest" as used herein, preferably, means one or more than one, e.g. at least two, at least three, at least four, at least five, at least six, at least seven or at least ten, or at least twenty polynucleotide(s) of interest, preferably the term "at least one polynucleotide of interest" means one polynucleotide of interest. Preferably, the polynucleotides of the methods of the present invention and the polynucleotide of interest are cointroduced (simultaneously introduced) into the host cell. The polynucleotides of the present invention may be introduced into a host cell by any technique suitable for introducing polynucleotides into a host cell which techniques are well known and well described in the art. For example, a polynucleotide can be introduced by electroporation, or by microinjection, or in a precipitate such as a calcium phosphate precipitate or rubidium chloride precipitate, or by lipid-based transfection, or in a complex with a charged lipid or in carbon-based clusters, such as fullerens. Moreover, a polynucleotide can be integrated by using viruses such as retroviruses. The polynucleotide(s) of the invention may be introduced into any host cell, preferably into any host cell which is mentioned in the context of this application. More preferably, the polynucleotides are introduced into a CHO cell by lipid-based transfection. The polynucleotide of interest and the polynucleotide(s) according to the method of the invention which shall be introduced into a host cell may be located on the same nucleic acid molecule, e.g. a DNA or RNA vector or on different nucleic acid molecules. Preferably, the polynucleotide comprising a first nucleic acid sequence for a chromatin element capable of enhancing expression and at least one second nucleic acid sequence comprising a curved origin motif and the polynucleotide of interest are on different nucleic acid molecules. Moreover, the polynucleotides which shall be introduced into a host cell may be present in a linear or circular form. The terms "linear" or "circular" in respect to nucleic acid molecules, particularly, DNA molecules, are understood by the skilled person. Preferably, the polynucleotide comprising a first nucleic acid sequence for a chromatin element capable of enhancing expression and at least one second nucleic acid sequence comprising a curved origin motif is present in linear form, and the polynucleotide of interest or any other polynucleotide (e.g. a polynucleotide encoding a marker) is present in a circular foam, e.g. on a plasmid. More preferably, the polynucleotide comprising a first nucleic acid sequence for a chromatin element capable of enhancing expression and at least one second nucleic acid sequence comprising a curved origin motif is present in linear form, and the polynucleotide of interest or any other polynucleotide (e.g. a polynucleotide encoding a marker) is present in a linear form, e.g. on a linearised plasmid It is to be understood that in accordance with the methods of the present invention, the expression of the polynucleotide of interest shall, preferably, be enhanced compared to the expression of the polynucleotide of interest in a reference host cell. Such a reference cell could be generated by introducing the polynucleotide of interest but not a polynucleotide of the invention (e.g. transfection of the polynucleotide of interest without a polynucleotide comprising a first nucleic acid sequence for a chromatin element, which is capable of enhancing expression, and at least one second nucleic acid sequence comprising a curved origin motif). Enhanced expression can be shown by means and methods as described herein above.

The term "cultivating said host cell(s)" as used herein relates to methods and means of cultivating cell under suitable conditions. Suitable conditions for cultivating cells are well known and well described in the art. Preferably, cultivation allows the cells to propagate, also referred to as growing, and to express the polynucleotide of interest. For example, a medium used for cultivation may be a medium which allows for minimal growth rates (a minimal medium) or a medium which allows for higher growth rates. Moreover, the composition of the medium may allow for selecting against a subpopulation of organisms/host cell. Preferably, due to selection only host cells that harbour an introduced selectable marker gene and that express the selectable marker gene in a sufficient amount may grow. A selection may be achieved by adding selecting agents, e.g. certain antibiotics, to the medium used for cultivation or by not adding substances, e.g. certain nutrients to the medium. Selecting agents which may be used in accordance to the methods of the present invention are aminoglycoside antibiotica which are inactivated by the enzyme neomycin phosphotransferase, preferably Geneticin (G418). Accordingly, selectable marker genes which may be used in the context of the aforementioned method are: neomycin phosphotransferase, hygromycin phosphotransferase, puromycin-N-acetyl-transferase, dihydrofolate reductase, glutamine synthetase, aspartate transcarbamylase, metallothionein, adenosine deaminase, adenylate deaminase, UMP synthetase, P-glycoprotein (p-gp, MDR), asparagines synthetase or ornithine decarboxylase. As described herein below, the marker gene may be a gene encoding a selectable marker protein having a reduced selection potential. Preferably, as mentioned above, the host is a CHO cell. Preferably, the CHO cells are grown in Ham's F-12 medium with L-glutamin (e.g. supplied by PAA Laboratories GmbH) with 10% fetal bovine Serum (FBS) at 37° C. in 5% CO2 atmosphere. Sub-confluent cultures (70-80%) were split 1:4 to 1:10 i.e. seeding at 1-2×10,000 cells/cm2 using 0.25% trypsin/EDTA (PAA Laboratories GmbH). It is to be understood that the cultivation of cells may include further steps such as isolating and subsequent propagating individual cells, particularly of high expressing cells.

Advantageously, it has been found in accordance with the aforementioned method of the present invention that the cointroduction of a polynucleotide comprising a first nucleic acid sequence for a chromatin element capable of enhancing expression and at least one second nucleic acid sequence comprising a curved origin motif, and of a polynucleotide of interest into a host cell enhances the expression of the polynucleotide of interest. For example, a polynucleotide comprising the AT rich region of the MII region of Intron 13 of the human topoisomerase I (Romig, 1994, Eur J Biochem. 221: 411-419) and an additional curved origin motif was cotransfected (i.e. cointroduced) together with the pEGFP-N1 vector (Clontech) comprising a reporter gene EGFP (Enhanced Green Fluorescent Protein (Chinese Hamster Ovary) and a NPT resistance gene. As controls, (a) the vector pEGFP-N1 alone, or (b) the vector in combination with DNA for a the AT rich region of the MII region of Intron 13 of the human topoisomerase I without an additional curved origin motif, were introduced into CHO cells. After a cultivation step which included a selection with G418 (0.6 mg/ml), reporter gene expression of individual cells was quantified by FACS analysis (Fluorescent Activated Cell Sorting). It has been found that compared to the controls the proportion of high-expressing cells, and thus the expression was significantly increased in CHO cells that were generated by cointroducing the reporter gene and said AT rich region comprising an additional curved origin motif. Thus, cointroducing a polynucleotide of interest (here a reporter gene) and DNA encoding said AT rich region which is capable of enhancing expression comprising a curved origin motif allows for high and stable expression of a polynucleotide of interest. Thus, the insertion of a curved origin motif into a chromatin element which per se is capable of enhancing expression of a cotransfected polynucleotide of interest further enhances the expression enhancing effect of said chromatin element.

The surprising effect of significantly enhanced and reliably stable expression was shown, e.g. for polynucleotides having a nucleic acid sequence as shown in SEQ ID NO:3 and SEQ ID NO:4, after cotransfection with a reporter gene and selection of resistant cells. Thus, the method of the present invention will reduce the time- and cost-intensive screening step for single high producing clones.

The present invention also relates to a method for expressing at least one polynucleotide of interest, comprising
(a) introducing into host cells
(i) at least one polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16, and
(ii) at least one polynucleotide of interest, and
(b) cultivating said host cells.

The aforementioned method comprises the cointroduction of at least one polynucleotide of interest and at least one polynucleotide according to the invention which encodes for a modified neomycin phosphotransferase gene into a host cell. The terms "introducing into a host cell", "host cell", "at least one polynucleotide of interest" have already been described herein above. Cultivating said host cell in the context of the aforementioned method means that the host cells are incubated under suitable cultivation conditions (see above). In case of the aforementioned method, the selectable marker gene is a neomycin phosphotransferase, the selecting agent may be an aminoglycoside antibiotic which is inactivated by the enzyme neomycin phosphotransferase. Preferably, the selecting agent is G418.

In accordance with the aforementioned method it is to be understood that the expression of the polynucleotide of interest in host cell shall be enhanced compared to a reference host cell. Preferably, in the context of the aforementioned method, a reference host cell is a host cell which expresses a corresponding polynucleotide of interest that was cointroduced with an unmodified NPT II gene.

Moreover, it is to be understood in the context of the aforementioned method that the polynucleotide encoding NPT II and the polynucleotide of interest may be located on the same nucleic acid molecule or on different nucleic acid molecules before introducing into a host cell. Preferably, the polynucleotide encoding the selectable marker and the polynucleotide of interest are on one molecule.

Advantageously, in accordance with the present invention it has been found that the use of polynucleotides encoding a NPT II mutant polypeptide as described elsewhere in this specification (i.e. a polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16) as a selectable marker gene for the transformation of CHO cells enhances the expression of a cointroduced reporter gene. DNA sequences comprising the aforementioned nucleic acid sequences were cointroduced into CHO cells with a EGPF reporter gene. After transfection, the cells were grown in medium containing G418. Comparative experiments were carried out in which instead of a polynucleotide according to the invention encoding a modified neomycin phosphotransferase, an unmodified NPT II gene (nucleic acid sequence as shown in SEQ ID NO:17) was used as a selectable marker gene. It has been found that reporter gene expression was significantly enhanced in a large portion of host cells transfected with a modified NPT II compared to the majority of host cells transfected with the unmodified marker. Thus, the aforementioned method according to the invention will even reduce the time- and cost-intensive screening steps for single high producing clones.

The present invention also relates to a method for expressing at least one polynucleotide of interest, comprising
(a) introducing into host cells
(i) at least one polynucleotide encoding a selectable marker having a reduced selection potential, and
(ii) at least one polynucleotide comprising a nucleic acid sequence capable of enhancing gene expression, and
(iii) at least one polynucleotide of interest, and
(b) cultivating said host cells.

The term "a nucleic acid sequence capable of enhancing gene expression" comprises any nucleic acid sequence which is capable of enhancing expression of a cotransfected polynucleotide of interest such as an enhancer, a MAR, SAR or UCOE sequence which is capable of enhancing expression of a cotransfected polynucleotide of interest, preferably the polynucleotide comprising a nucleic acid sequence capable of enhancing gene expression is a polynucleotide comprising a nucleic acid sequence for a chromatin element, which is capable of enhancing expression, more preferably the polynucleotide comprising a nucleic acid sequence capable of enhancing gene expression is a polynucleotide as specified above comprising a first nucleic acid sequence for a chromatin element, which is capable of enhancing expression, and at least one second nucleic acid sequence comprising a curved origin motif as described herein above, most preferably the polynucleotide comprising a nucleic acid sequence capable of enhancing gene expression is a polynucleotide comprising a nucleic acid sequence as shown in SEQ ID NO:3, in SEQ ID NO:4, in SEQ ID NO:5, or in SEQ ID NO:6. It is to be understood in the context of the aforementioned method that the polynucleotide comprising a nucleic acid sequence capable of enhancing gene expression may comprise or may not comprise an additional curved origin motif.

The term "selectable marker having a reduced selection potential" as used herein relates to a genetically modified selectable marker whose selection potential is reduced compared to the respective unmodified marker (e.g. the wild-type). WO 2004/050884 discloses markers having a reduced selection potential for enhancing the expression of cotransfected polynucleotides of interest. Under reduced selection potential it is to be understood, that the enzyme activity of the marker protein is reduced. Enzyme activity may be reduced by modifying the amino acid sequence of a marker gene protein, e.g. by mutating the polynucleotide sequences encoding for said marker protein. Enzyme activity can be determined by enzyme assays which are well known and well described in the art. All enzyme assays measure either the consumption of suitable substrate or production of product over time. A large number of different methods of measuring the concentrations of substrates and products exist and many enzymes can be assayed in several different ways. Enzyme assays as meant herein may be carried out by the following approaches: Initial rate experiments, progress curve experiments, transient kinetics experiments, relaxation experiments. The consumption of the suitable substrate or the production of product can be determined by spectrophotometric means, fluorometric means, calorimetric means or chemiluminescent means, radiometric means and chromatographic means. The assays can be done continuously (production or consumption is continuously determined) or discontinuously (samples are taken in intervals). In order to compare enzyme activities, the activity of a first enzyme (e.g. a modified marker protein) is compared to the enzyme activity of a second enzyme (e.g. an unmodified marker protein) under the same conditions. The enzyme may have been purified or be a component of a cell extract. Preferably, the enzyme activity of the selectable marker having a reduced selection potential in the context of the aforementioned method is 1-80% reduced, more preferably 1-50% reduced, most preferably 1-20% reduced when compared to the enzyme activity of the unmodified selectable marker. The reduced selection potential can be achieved by modifying the nucleic acid sequence of a wild-type marker gene, so that the corresponding amino acid sequence has at least one amino acid change compared to the respective amino acid sequence of the wild-type marker. The term "at least one amino acid change" as used here, preferably, means one or more than one amino acid changes, e.g. at least two, at least three, at least four, at least five, at least six, at least seven or at least ten, at least twenty, at least thirty, at least forty, at least fifty, or at least one hundred. In the context of the present invention the reduced selection potential may also be caused by using an expression control sequence, e.g. a promoter, which confers reduced expression of the selectable marker gene compared to other expression control sequences. In accordance with the aforementioned method of the present invention selectable marker genes may be neomycin phosphotransferase, hygromycin phosphotransferase, puromycin-N-acetyl-transferase, dihydrofolate reductase, glutamine synthetase, aspartate transcarbamylase, metallothionein, adenosine deaminase, adenylate deaminase, UMP synthetase, P-glycoprotein (p-gp, MDR), asparagines synthetase or ornithine decarboxylase.

In a preferred embodiment of the aforementioned method, the polynucleotide encoding a selectable marker is a polynucleotide encoding for a modified neomycin phosphotransferase. Modified neomycin phosphotransferases genes which may be used in the aforementioned method are described, e.g., in WO 2004/050884, which is herewith incorporated by reference in its entirety.

In another more preferred embodiment of the aforementioned method, the polynucleotide encoding a selectable marker having a reduced selection potential is a polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16. Most preferably, said polynucleotide is a polynucleotide encoding a polypeptide comprising an amino acid sequence as shown in SEQ ID NO:13, or is a polynucleotide comprising a nucleic acid sequence as shown in SEQ ID NO:16. Also contemplated as polynucleotides encoding a selectable marker having a reduced selection potential for the method of the present invention are polynucleotides encoding modified NPT II polynucleotides having, compared to the wild-type NPT II (see SEQ ID NO:35), an amino acid substitution of E to D at amino acid position 182, of D to G at position 190, of D to G at position 208, of D to G at position 227, of E to G at position 182, of W to A at position 91, of V to G at position 198, of D to A at position 227, of D to V at position 227, of D to G at position 261, of D to N at position 261, or of F to I at position 240 of the wild-type NPT II polypeptide (all of which are disclosed by Sauter, BIOTECHNOLOGY AND BIOENGINEERING, VOL. 89, NO. 5, 2005). Further preferred are polynucleotides encoding modified NPT II polypeptides having, compared to the wild-type NPT II polypeptide, an amino acid substitution at position V to M at position, E to D at position 182, G to E at position 205, G to A at position 210, R to P at position 211, R to K at position 211, R to H at position 211.

Advantageously, it has been found in accordance with the present invention that the cointroduction of a polynucleotide encoding a modified NPT II selectable marker gene, and a polynucleotide comprising a nucleic acid sequence capable of enhancing gene expression, and a polynucleotide of interest into a host cell significantly enhances the expression of the polynucleotide of interest. E.g., a polynucleotide encoding a modified NPT II marker comprising an amino acid sequence as shown in SEQ ID NO:13, a polynucleotide comprising the AT rich region of the MII region of Intron 13 of the human topoisomerase I (Romig, 1994, Eur J Biochem. 221:411-419) and an additional curved origin motif (nucleic acid sequence as shown in, e.g. in SEQ ID NO:3) and the reporter gene EGFP were cointroduced into CHO cells (Chinese Hamster Ovary). As controls, a) the vector pEGFP-N1 harbouring an EGFP gene and an unmodified NPT II gene, or b) the pEGFP-N1 vector in combination with DNA for the corresponding AT rich region of the MII region of Intron 13 of the human topoisomerase I comprising a curved origin motif (SEQ ID NO:3), were introduced into CHO cells. In addition, a modified NPT II gene as described by Sautter and Enekel (mutant D227V, Sautter and Enekel, Biotechnology and Bioengineering, 89, (2005) 530-538) in combination with DNA for the corresponding AT rich region of the MII region of Intron 13 of the human topoisomerase I with an additional curved origin motif (SEQ ID NO:3) were cointroduced with a reporter gene in CHO cells. After transfection, resistant cells were selected during cultivation in medium containing G418. Reporter gene expression of individual G418 resistant host cells was quantified by FACS analysis (Fluorescent Activated Cell Sorting). It has been found that compared to the controls, the proportion of high expressing cells and, thus, the expression was significantly increased in CHO cells that were generated by cointroducing the EGFP gene, the polynucleotide comprising said AT rich region and a curved origin motif, and the polynucleotide encoding a modified NPT II selectable marker gene. Moreover, the use of the modified NPT II D227V mutant enhances the expression of the polynucleotide of interest compared to the use of an unmodified NPT gene, however the use of a modified NPT II D227V gene resulted in a significantly lower gene expression level than the modified NPT II marker comprising an amino acid sequence as shown, e.g., in SEQ ID NO:13.

Thus, cointroducing of least one polynucleotide encoding a selectable marker having a reduced selection potential like a polynucleotide encoding a modified NPT II, at least one polynucleotide comprising a nucleic acid sequence capable of enhancing gene expression like a polynucleotide as specified above comprising a first nucleic acid sequence for a chromatin element, which is capable of enhancing expression, and at least one second nucleic acid sequence comprising a curved origin motif, and a polynucleotide of interest into host cells and cultivating said cells using a suitable selection agent, significantly enhances the expression of the polynucleotide of interest. Moreover, this effect was not only shown for CHO cells but also for reptile cells (viper cell line VH2). The enhancing effect on expression of the combined introduction of the polynucleotides of the invention into host cells is larger than the effect of the individual components alone, or even the sum of the individual effects, thus, said combined introduction shows an unexpected synergism. Using a modified NPT II marker, e.g. having an amino acid sequence as shown, in SEQ ID NO:13 resulted after selection with G418 in resistant clones, of which the majority were high producing clones, whereas the majority of low producing clones presumably was lost during selection procedure.

Thus, the aforementioned method allows an effective and fast procedure for isolating high producers and reduces the necessity of cost and time intensive gene amplification and screening steps.

Moreover, the cells generated as described above showed a surprisingly stable expression of the polynucleotide of interest. Single clones were isolated from resistant colonies consisting of cells which were generated as described above [by cotransfecting a polynucleotide encoding a modified NPT II marker (e.g. comprising an amino acid sequence as shown in SEQ ID NO:13), a polynucleotide comprising the AT rich region of the MII region of Intron 13 of the human topoisomerase I and a curved origin motif having a nucleic acid sequence as shown, e.g. in SEQ ID NO:3, and cultivation under selection pressure] and were cultivated continuously for 8 weeks without selection pressure. Surprisingly, a FACS analysis after eight weeks cultivation without selection pressure showed that 50% of tested clones had unchanged reporter gene expression while the other 50% of clones showed a slightly reduced reporter gene expression compared to the reporter expression at the beginning of the 8 week cultivation (50%-90% of the expression at the beginning). Thus, the aforementioned method advantageously allows for a time efficient production of clones with a strong and stable expression of the polynucleotide of interest even in the absence of a selectable marker agent.

In a preferred embodiment of the methods of the present invention the host cell may be cultivated in serum-free medium or serum-containing medium. More preferably, the host cell is cultivated in serum-free medium. It is advantageous to culture the host cell in a serum-free medium since the risk of infection resulting from cultivation in serum-containing medium can be reduced. Moreover, using a serum-free medium is more cost-effective, specifically for large scale approaches. The meaning of the term "serum" is well understood by the one skilled in the art. The term "serum-free medium" as used herein means a growth medium for cultivating any host cell that does not comprise serum of any type, e.g. fetal bovine serum or any serum components such as proteins separated from serum. In contrast, the serum-containing medium as meant herein relates to medium that contains serum or serum components such as proteins separated from serum.

In another embodiment of the methods of the invention the polynucleotide of interest encodes a polypeptide which is selected from the group consisting of immunoglobulins, such as humanized antibodies, therapeutic proteins, membrane proteins and enzymes, hormones, ion channels proteins and proteases.

Moreover the invention relates to a method for the manufacture of a polypeptide of interest comprising the steps of any of the aforementioned methods and the further step of obtaining the polypeptide encoded by the polynucleotide of interest.

In another more preferred embodiment of the methods of the invention the host cell is an animal cell, a plant cell, a yeast cell, a fungal cell and an algae cell. More preferably, said cell is a mammalian or vertebrate cell. Most preferably, as mentioned above, the host cell is a CHO cell. Also contemplated by the present invention are reptilian cells, preferably viper cells preferably the cell line VH2 (Viper Russells heart, ECACC No. 90102539)

Moreover, the present invention relates to a pharmaceutical composition comprising a polynucleotide comprising a first nucleic acid sequence for a chromatin element, which is capable of enhancing expression, and at least one second nucleic acid sequence comprising a curved origin motif and/or a polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16. Moreover, the pharmaceutical composition may comprise a polynucleotide of interest encoding for a product having a therapeutic effect.

The term "pharmaceutical composition" as used herein comprises the compounds of the present invention and optionally one or more pharmaceutically acceptable carrier. The compounds of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. However, depending on the nature and mode of action of a compound, the pharmaceutical compositions may be administered by other routes as well. For example, polynucleotide compounds may be administered in a gene therapy approach by using viral vectors or viruses or liposomes.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days.

Moreover, the present invention relates to the use of a polynucleotide comprising a polynucleotide comprising a first nucleic acid sequence for a chromatin element, which is capable of enhancing expression, and at least one second nucleic acid sequence comprising a curved origin motif and/or a polynucleotide encoding a polypeptide comprising an amino acid sequence as shown in any one of SEQ ID NO:11, SEQ ID NO:12 and SEQ ID NO:13 or comprising a nucleic acid sequence as shown in any one of SEQ ID NO:14, SEQ ID NO:15 and SEQ ID NO:16 for the manufacture of a pharmaceutical composition to be used for gene therapy.

The term "gene therapy" as used herein is to be understood as a method for treatment in which at least one polynucleotide of the invention is introduced into a host cell of a subject either in vivo or by introduction into a host cell in vitro followed by re-implantation into a subject (e.g. a human or non-human animal). Preferably, the polynucleotide of the invention is co-introduced into a host cell to be used for gene therapy together with a polynucleotide of interest, which, preferably encodes for a product of interest having a therapeutic effect. "Gene therapy" as used herein may mean that a polynucleotide of interest is introduced into a cell in order to compensate for lack of function of a host gene. Moreover, an abnormal gene may be replaced by a functional gene through homologous recombination. Moreover, the regulation, i.e. the expression of a particular gene may be altered, e.g. by regulatory RNA, e.g. in an RNAi approach. Preferably, introduction is carried out by techniques well known in the state in the art. More preferably, the introduction is carried out by use of viral vectors. For this purpose, the viral vectors may be genetically altered by removing viral disease causing genes and by inserting the abovementioned polynucleotides. Viral vectors include, but are not limited to, retroviruses, adenoviruses, adeno-associated viruses. The aforementioned polynucleotides may also be delivered by non-viral methods such as transfection with naked DNA or by use of liposomes. Diseases to be treated by gene-therapy may be, but are not limited to, cancer, neuronal diseases, metabolic diseases, immunodeficiency diseases. Emerging vectors and targeting methods for nonviral gene therapy are described by Lavigne and Gorecki (Expert Opinion of Emerging Drugs (2006) 11, 541-557)

All references cited in this specification are herewith incorporated by reference with respect to their entire disclosure content and the disclosure content specifically mentioned in this specification.

FIG. 1: Nucleic acid sequence of an AT rich region of intron 13 of human topoisomerase I comprising an inserted curved origin motif as shown in SEQ ID NO:3. The curved origin motif is underlined.

FIG. 2: Nucleic acid sequence of an AT rich region of intron 13 of human topoisomerase I comprising an inserted curved origin motif as shown in SEQ ID NO:4. The curved origin motif is underlined.

FIG. 3: Expression of the reporter gene EGFP in CHO cells after transfection with 100 ng circular pEGFP-N1 alone (indicated by an "o"), or cotransfection of 100 ng circular pEGFP-N1 vector (Clontech) and 100 ng linear DNA comprising the AT rich region of the MII region of Intron 13 of the human topoisomerase I comprising a nucleic acid sequence as shown in SEQ ID NO:27 (indicated by an "X"), or cotransfection of 100 ng circular pEGFP-N1 vector (Clontech) and a 100 ng linear DNA encoding a AT rich region of the MII region of Intron 13 of the human topoisomerase I as shown in SEQ ID NO:28 (●), or 100 ng circular pEGFP-N1 vector (Clontech) and a 100 ng linear DNA comprising the AT rich region of the MII region of Intron 13 of the human topoisomerase I comprising a curved origin motif as shown in SEQ ID NO:3 (■). The vector pEGPF-N1 comprises the EGPF reporter gene and a wild-type NPT II gene. After cultivation for approximately eight weeks under selection pressure (0.6 mg/ml G418) reporter gene expression of individual cells was quantified by FACS analysis (sensitivity of fluorescence detection: 4 decades, gain 300). The proportion of cells with a relatively strong reporter gene expression is significantly enhanced when the cells were cotransfected with a chromatin element which is capable of enhancing expression comprising a curved origin motif compared to cells which were transformed with pEGPF-N1 alone or with pEGPF-N1 and a chromatin element with is capable of enhancing expression without a curved origin motif.

Figure 4:
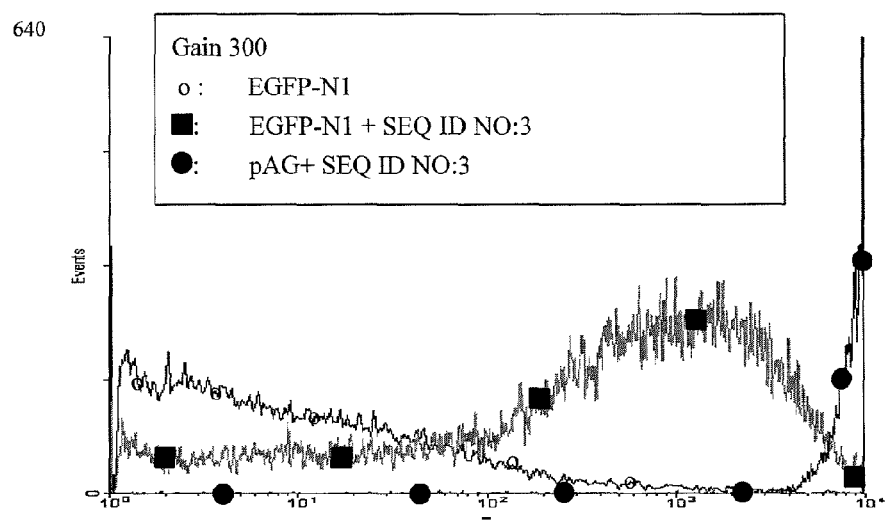

FIG. 4: Expression of EGFP in CHO cells after transfection with either 90 ng DNA of linearized pEGFP-N1 alone (indicated by an "o"), or cotransfection of 90 ng linearized pEGFP-N1 and 300 ng DNA for the AT rich region of the MII region of Intron 13 of the human topoisomerase I and an additional curved origin motif (nucleic acid sequence as shown in SEQ ID NO:3) (■), or cotransfection of 90 ng of a vector (pAG) harbouring a EGFP reporter gene and a modified neomycin phosphotransferase comprising a nucleic acid sequence as shown in SEQ ID NO:16 and 300 ng of DNA encoding the AT rich region of the MII region of Intron 13 of the human topoisomerase I and an additional curved origin motif with a nucleic acid sequence as shown in SEQ ID NO:3 (●). After cultivation for approximately eight weeks under selection pressure (0.6 mg/ml G418) reporter gene expression of individual cells was quantified by FACS analysis (Instrument settings: gain of optical detector=300, amplification mode=4 decade logarithmic). The proportion of cells showing a strong reporter gene expression was significantly higher when the reporter gene was introduced into CHO cells in combination with DNA encoding the AT rich region of Intron 13 of human topoisomerase I with an additional a curved origin motif than when pEGFP-N1 was transfected alone. Moreover, the proportion of cells with a strong reporter gene expression was highest, when both a the AT rich region of intron 13 of human topoisomerase I comprising a curved origin motif and DNA encoding a modified neomycin phosphotransferase gene (localized on the pEGFP-N1 plasmid, instead of the unmodified neomycin phosphotransferase) were introduced into the CHO cells. The stable expression in cells which have been transfected with the modified neomycin phosphotransferase having a nucleic acid sequence as shown in SEQ ID NO:16 and the AT rich region comprising a curved origin motif (nucleic acid sequence as shown in SEQ ID NO:3) was unexpectedly high so that the range of fluorescence detection was not sufficient for detecting low and high expressing cells simultaneously. Because of the difference in fluorescence intensity between low and high expressing cells being greater than a factor of 10sup.4, cells were measured again using a lower sensitivity (FIG. 5 Instrument settings: gain of optical detector=200, amplification mode=4 decade logarithmic).

Figure 5:
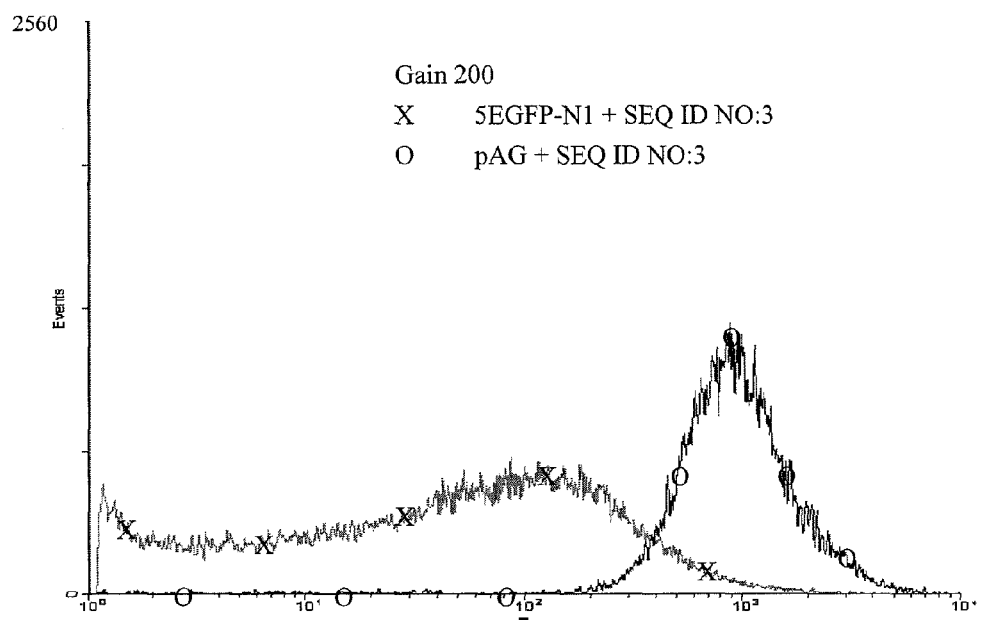

FIG. 5: Populations of CHO cells transfected and selected as indicated in the figure legend of FIG. 4. Sensitivity of fluorescence detection (4 decades) measured with a gain of 200. The majority of CHO cells cotransfected with pAG and AT rich region (nucleic acid sequence as shown in SEQ ID NO:3) ("O") showed an approximately 10 fold higher expression than CHO cells cotransfected with pEGFP-N1 and AT rich region (nucleic acid sequence as shown in SEQ ID NO:3 (indicated with an "X").

Thus, the proportion of cells with a strong reporter gene expression was significantly enhanced when both DNA for the AT rich region of Intron 13 of human topoisomerase I with an additional curved origin motif and DNA encoding a modified neomycin phosphotransferase gene were introduced into the CHO cells.

Figure 6:
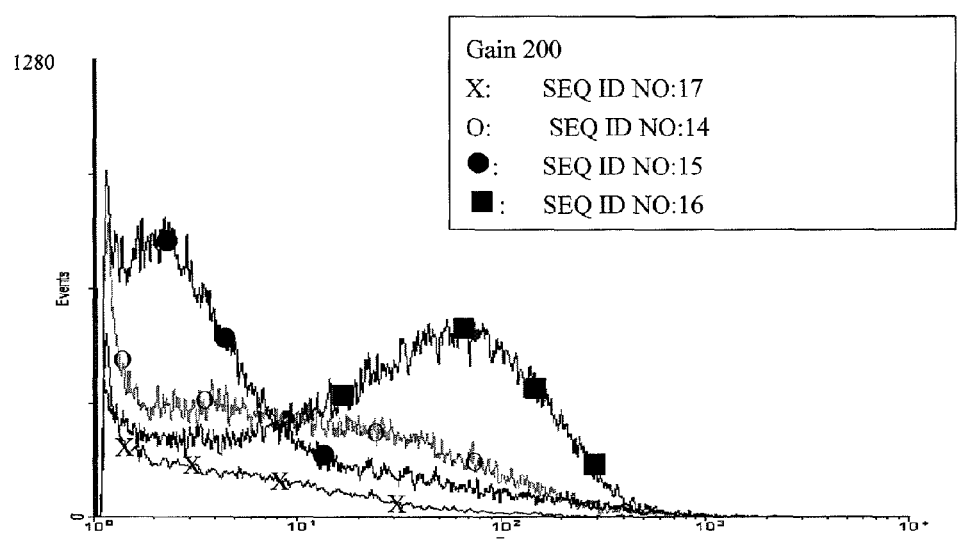

FIG. 6: Expression of EGPF in CHO cells after transfecting the reporter gene EGFP in combination with various neomycin phosphotransferase resistance genes (NPT II) and selection as indicated in figure legend of FIG. 3. The effect of the following neomycin phosphotransferase resistance genes on the expression of a the cotransfected reporter gene was analysed: the unmodified NPT II gene comprising a nucleic acid sequence as shown in SEQ ID NO:17 (indicated with an "X"), as well as modified NPT II genes comprising a nucleic acid sequence as shown in SEQ ID NO: 14 (indicated with an "O"), SEQ ID NO:15 (●), SEQ ID NO:16 (■), respectively. Reporter gene expression of individual cells was determined by FACS analysis after eight week cultivation in selection medium containing sufficient amounts of G418). The proportion of cells showing a relatively strong expression of the reporter gene was significantly higher for cells which were transfected with a modified neomycin phosphotransferase compared to cells which were transfected with the wild-type neomycin phosphotransferase. The proportion of cells showing a relatively strong expression of the reporter gene was highest for cells which were transfected with a modified neomycin phosphotransferase having the nucleic acid sequence as shown in SEQ ID NO:16.

Figure 7:
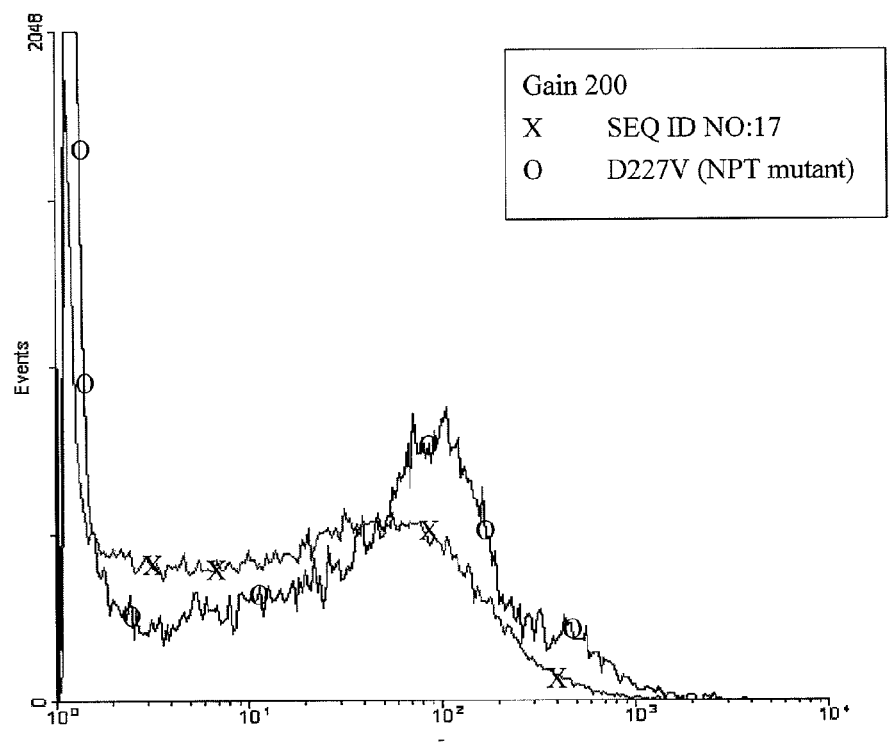

FIG. 7: Expression of EGPF in CHO cells after cotransfecting the reporter gene EGFP in combination with a modified neomycin phosphotransferase resistance gene D227V (SEQ ID NO:36) (O) and DNA for AT rich region of the MII region of Intron 13 of the human topoisomerase I with an additional curved origin motif (SEQ ID NO:3). As a control an unmodified neomycin phosphotransferase (pEGFP-N1) was cotransfected with DNA for the AT rich region of the MII region of Intron 13 of the human topoisomerase I with an additional curved origin motif (SEQ ID NO:3) (X). Cells were cultivated, transfected with FuGENE 6 and selected with G418 medium as described in Example 3. After cultivation for 6 weeks in medium supplemented with 0.6 mg/ml G418, gene expression of individual cells was determined by FACS analysis as described in Example 3 (Instrument settings: gain of optical detector=200, amplification mode=4 decade logarithmic) (FIG. 7). Although the described modified NPT II D227V mutant cotransfected with the AT rich region (SEQ ID NO:3) enhances the expression of the polynucleotide of interest relatively to the unmodified NPT gene cotransfected with the AT rich region (SEQ ID NO:3), the increase was less than for cointroducing a modified neomycin phosphotransferase of the present invention, which e.g., has a nucleic acid sequence as shown in SEQ ID NO:16.

The following Examples shall merely illustrate the invention. They shall not be construed, whatsoever, to limit the scope of the invention.

EXAMPLE 1

Generation of a MAR Sequence with a Curved Origin Motif

Genomic DNA was purified from human leukozytes and from HeLa cells by using the "Blood & Cell Culture DNA Kit" (QIAGEN GmbH, Hilden, Germany) according to the manufacturer's instructions. An AT-rich region of the MII region of Intron 13 of the human topoisomerase I (Romig, Eur J Biochem. 221:411-419) was amplified by two subsequent PCR reactions (nested PCR) using approximately 200 ng of genomic DNA extracted from HeLa cells or extracted from human blood as a template, the Pfu polymerase as a polymerase and the following primers:

```
Primer 1 (‚forward'):
5'-CCAGCTAACTGCTATACACAATAGACATTTGTGC (as shown in
SEQ ID NO: 61)

Primer 2 (‚reverse'):
5'-CTGCCAACAGTAATTAGCACATGAATTCACTTCAGGTAAC (as
shown in SEQ ID NO: 62)
``` and for the second PCR

```
Primer 3 (‚forward'):
5'-GTGCCTGACTTGAACTGCAATGGG (as shown in SEQ ID
NO: 63)

Primer 4 ('reverse'):
5'-CAGTAATTAGCACATGAATTCAC (as shown in SEQ ID
NO: 64)
```

Underlined is a sequence for an EcoRI restriction site which was used for a later cloning step.

The first PCR reaction was performed as follows: 30 cycles of 2 min denaturation at 94° C., annealing at 50° C. for 35 seconds and 2 min elongation at 72° C., followed by 5 min final elongation at 72° C.

The second PCR was performed using a portion of the first PCR as template: 30 cycles of denaturation for 1 minute at 94° C., annealing at 50° C. for 35 seconds and 2 min elongation at 72° C., followed by 5 min elongation at 72° C.

In a following step, the PCR product was ligated into the SrfI site (SrfI creates blunt ends) of the vector pPCR-Script-Amp-SK(+) (Stratagene, La Jolla, USA) by using the PCR-Script® Amp Cloning Kit according to the manufacturer's instructions. After ligation, the ligation product was transformed into competent *E. coli* cells (XL-Gold Kan, PCR-Script® Amp Cloning Kit) according to the instructions of the manufacturer. After transformation, cells were incubated for approximately 20 h at 37° C. on Luria-Broth-Medium that was supplemented with 100 µg/ml Ampicillin in order to allow selection for successfully transformed cells. Subsequently, a 2.9 kb BamH1/EcoR1 Blood AT-rich nucleic acid fragment and a. 2.9 kb BamH1/EcoR1 HeLa AT rich nucleic acid fragment of the resulting vector harbouring the PCR fragment were cloned into the BamH1/EcoR1 restriction site of the vector pUC18. The cloned PCR products were designated "Blood AT-rich nucleic acid" (originally amplified from genomic DNA extracted from blood; nucleic acid sequence as shown in SEQ ID NO:28) and "HeLa AT rich nucleic" (originally amplified from genomic DNA extracted from HeLa cells; nucleic acid sequence as shown in SEQ ID NO:27). Both AT-rich sequences show a high sequence identity but have sequence differences at some positions (position 613, 1079-1082, 1128, 1160-1163, 1176, 1188, 1197, 1205, 1227, 1236, 1333, 1905, 1919, 1931, 1950, 1959, 1975, 2191, 2234, 2495, 2507, 2634, 2652, 2733, 2762 and 2768). By site directed mutagenesis a restriction site for the restriction endonuclease AvrII was introduced into both the HeLa and the Blood AT rich nucleic acid sequence using the QuickChange® site directed mutagenesis kit (Stratagene) according to the manufacturer's instructions. (Nucleic acid sequences of the primers used for site directed mutagenesis:

```
Primer avr_sense
ggtcttgtatctgcctaggagatacaagaggtgctc (as shown in
SEQ ID NO: 65)

Primer avr_asense
gagcacctcttgtatctcctaggcagatacaagacc (as shown in
SEQ ID NO: 66)
```

The curved origin motif was synthesized by Geneart AG (Regensburg) using a method as described in Nálezkováa et al (2005) Protein Expression and Purifikation 39, 296-306.

An AvrII fragment comprising the curved origin motif was cloned in both orientations into the newly created AvrII restriction site of the HeLa- and Blood AT-rich sequence. The nucleic acid sequences of the four resulting constructs are shown in SEQ ID NO:3, SEQ ID NO:4, SEQ ID NO:5 and SEQ ID NO:6.

EXAMPLE 2

Generation of Polynucleotides Encoding a Modified Neomycin Phosphotransferases II (NPT II)

NPT II polynucleotides encoding a modified NPT II protein having 1 or 2 amino acid changes were generated by site directed mutagenesis using the using the vector pEGFP-N1 harboring an unmodified NPT II (wild-type) gene as a template. The following primer pairs were used for the site directed mutagenesis using the QuickChange® site directed mutagenesis kit (Stratagene) according to the manufacturer's instructions:

```
For the NPTII R226A mutant (resulting nucleic acid
sequence as shown in SEQ ID NO: 14)
R226A_sense:
catagcgttggctaccgctgatatcgctgaagagcttggc (as shown
in SEQ ID NO: 67)

R226A_asense:
gccaagctcttcagcgatatcagcggtagccaacgctatg (as shown
in SEQ ID NO: 68)

For the R226V mutant (resulting nucleic acid
sequence as shown in SEQ ID NO: 15)
R226V_sense:
catagcgttggctaccgttgatatcgctgaagagcttggc (as shown
in SEQ ID NO: 69)

R226V_asense:
gccaagctcttcagcgatatcaacggtagccaacgctatg (as shown
in SEQ ID NO: 70)

For the NPTII A224G: T2255 double mutant (re-
sulting nucleic acid sequence as shown in SEQ ID
NO: 16)
A224G_sense:
ctatcaggacatagcgttgggatcccgtgatattgctgaagagc (as
shown in SEQ ID NO: 71)

A224G_asense:
gctcttcagcaatatcacgggatcccaacgctatgtcctgatag (as
shown in SEQ ID NO: 72)

For the NPTII D227V mutant (resulting nucleic acid
sequence as shown in SEQ ID NO: 36)
D227V_sense:
ggacatagcgttggctacacgcgttattgctgaagagcttgg (as
shown in SEQ ID NO: 73)

D227V_asense:
ccaagctcttcagcaataacgcgtgtagccaacgctatgtcc (as
shown in SEQ ID NO: 74)
```

The resulting vectors comprise both the EGPP gene and a modified neomycin phosphotransferases II gene.

EXAMPLE 3

The Cointroduction of the AT Rich Region of Intron 13 of Human Topoisomerase I with an Additional Curved Origin Motif and a Reporter Gene into CHO Cells Significantly Enhances the Proportion of Cells Showing a High Reporter Gene Activity The effect of a polynucleotide comprising the AT rich region of intron 13 of human topoisomerase I and a curved origin motif on expression of a cotransfected reporter gene was analyzed. For this reason 100 ng pEGFP-N1 vector harbouring the reporter gene 5EGFP an unmodified neomycin phosphotransferase gene was transfected into CHO cells together with the following MAR constructs (100 ng each). AT rich nucleic acid as shown in SEQ ID NO:28 (Blood AT rich sequence)
AT rich nucleic acid as shown in SEQ ID NO:27 (HeLa AT rich sequence)
AT rich nucleic acid as shown in SEQ ID NO:3 (AT rich sequence with an inserted curved origin motif)
As a control, the pEGFP-N1 vector was transfected alone.
The CHO-K1 cell line was cultivated in Ham's F-12 with L-Glutamine (PAA Laboratories GmbH) supplemented with 10% FBS (PAA Laboratories GmbH). Pools of stable CHO cells expressing EGFP were obtained by transfection with FuGENE 6 (Roche) according to the manufacturer's instructions and a ratio DNA:FuGENE of 1:4 (μg DNA:μl FuGENE 6). Cells were seeded in 24-well plates at 100-200 000 cells/well and allowed to attach overnight. 100 ng pEGFP-N1 were cotransfected with 100 ng of linear AT rich sequence. The linear AT rich sequences (SEQ ID NO:3, SEQ ID NO:27, SEQ ID NO:28) were isolated after restriction digestion and gel electrophoresis by gel elution. After 48 hours, medium changes were carried out with medium supplemented with 0.6 mg/ml G418 (G418 sulfate, Calbiochem). Subsequent medium changes were carried out with medium supplemented with 0.6 mg/ml G418 with pools of clones assayed after eight weeks of selection. The reporter gene (EGFP) expression, i.e. the fluorescence of individual cells was quantified by FACS analysis using a PARTEC Flow Cytometer (Partec Analysing System PAS, Partec GmbH, Munster). Fluorescent events were acquired using a 530/15 bandpass filter for the green fluorescence protein signal. (Instrument settings: gain of optical detector=300, amplification mode=4 decade logarithmic).

The intensity of the reporter gene signal indicates the expression, i.e. a strong fluorescence signal indicates a high reporter gene expression. The numbers of individual cells having a specific fluorescence (also called events) was plotted against the level of fluorescence. The results of the various transfection experiments are shown in FIG. 3. If the vector harbouring the GPF gene was transfected into CHO cells alone, the majority of cells showed a relatively low reporter gene expression. If in addition to the vector DNA encoding the AT rich region of the topoisomerase gene (either the "Blood AT rich" construct, as shown in SEQ ID NO:28 or the "HeLa AT rich" construct, as shown in SEQ ID NO:27) was transfected into the cells, the proportion of cells showing a relatively high reporter gene expression was significantly enhanced compared to transfection of the vector alone. Unexpectedly, almost all cells cotransfected with AT rich sequences showed an EGFP expression. Presumably, only a very small amount of cells showed a gene silencing. In contrast nearly all cells of the G418 resistant cell pool transfected with the EGFP-N1 vector alone showed no EGFP expression at all. Thus only a very small amount of cells being transfected with the EGFP-N1 vector alone showed no gene silencing and this cell population was detected in FACS analysis with a fluorescence intensity between 10sup.1 and 10sup.2. Reporter gene expression was highest, when in addition to the pEGFP-N1 vector the AT rich region of human topoisomerase with an additional curved origin motif (nucleic acid sequence as shown in SEQ ID NO:3 was transfected into CHO cells. Expression was enhanced by a factor of approximately 10-20 (cotransfected SEQ ID NO:3) compared to cells which have been cotransfected with SEQ ID NO:28. Corresponding results were also observed for the AT rich constructs in which the curved origin was in an opposite direction (nucleic acid sequence as shown in SEQ ID NO:4. Thus, the transfection of a chromatin element (which alone is capable of enhancing expression) with an additional curved origin motif significantly increases the number of cells of a cell population showing a strong expression of a cotransfected gene compared to the cotransfection of a reporter gene and a chromatin element which does not comprise an additional curved origin motif.

EXAMPLE 4

The Use of a Modified Neomycin Phosphotransferase for Selecting Transfected CHO Cells Increases the Expression of a Reporter Gene Mutated neomycin phosphotransferase genes having 1 or 2 amino acid changes were prepared as described in Example 2. Vectors harbouring the modified neomycin resistance genes under control of the SV40 early promoter as well as the reporter gene EGFP under control of the Human cytomegalovirus (CMV) immediate early promoter were transfected into CHO cells. As a control, the vector pEGPP-N1 harbouring the unmodified neomycin phosphotransferase gene under control of the SV40 early promoter as well as the reporter gene EGFP under control of the Human cytomegalovirus (CMV) immediate early promoter was transfected into CHO cells. Cells were cultivated, transfected with FuGENE 6 and selected with G418 medium as described in Example 3. After cultivation, reporter gene expression of the transfected cells was analysed by FACS analysis. The reporter gene (EGFP) expression was quantified by FACS analysis using a PARTEC Flow Cytometer (Partec Analysing System PAS, Partec GmbH, Munster). Fluorescent events were acquired using a 530/15 bandpass filter for the green fluorescence protein signal. (Instrument settings: gain of optical detector=200, amplification mode=4 decade logarithmic) Results of the FACS analysis are shown in the graph of FIG. 6. The graph shows the number of cells (X-axis) plotted against the level of fluorescence emitted (Y-axis) by the cells. As clearly can be seen, the proportion of cells which show a very strong reporter gene activity is significantly higher when a modified neomycin phosphotransferase gene was used as a selectable marker. Reporter gene expression was less, when the selectable marker was an unmodified resistance gene. Particularly, the use of modified neomycin phosphotransferase having a nucleic acid sequence as shown in SEQ ID NO:16 resulted in a higher proportion of high-producing cells.

Summarized, the use of a modified selectable marker enhances the proportion of cells in a transfected cell population showing a relative strong expression of the reporter gene.

EXAMPLE 5

The Cointroduction of an AT Rich Sequence of Intron 13 of Human Topoisomerase I with an Additional Curved Origin Motif and a Gene Encoding for a Modified Neomycin Transferase into CHO Cells Significantly Enhances the Proportion of Cells Showing a High Reporter Gene Activity The effect of the cointroduction of a chromatin element capable of enhancing expression (here the AT rich sequence of intron 13 of human topoisomerase I) harbouring an additional curved origin motif (nucleic acid sequence as shown in SEQ ID NO:3) and a vector comprising a modified neomycin phosphotransferase (nucleic acid sequence as shown in SEQ ID NO:16) and the reporter gene EGPF (polynucleotide of interest) on reporter gene expression was analysed. As controls, a vector comprising the reporter gene and an unmodified neomycin phosphotransferase gene (nucleic acid sequence as shown in SEQ ID NO:17) was transfected into CHO cells, or a vector, comprising the reporter gene EGFP and an unmodified neomycin phosphotransferase gene (nucleic acid sequence as shown in SEQ ID NO:17), and DNA encoding the AT rich sequence of intron 13 of human topoisomerase with an additional curved origin motif (nucleic acid sequence as shown in SEQ ID NO:3) were cotransfected into CHO cells. For these experiments, cells were cultivated, transfected using FuGENE 6 (90 ng linearized plasmid and/or 300 ng AT rich sequence) and selected with G418 medium as described in Example 3. After eight weeks cultivation reporter gene expression of individual cells was determined by FACS analysis as described in Example 3 (Instrument settings: gain of optical detector=200 or 300, amplification mode=4 decade logarithmic). FIGS. 4 (gain of optical detector=300) and 5 (gain of optical detector=200) show the results for the expression analysis. The graphs therein show the number of cells (X-axis) and the level of fluorescence emitted (Y-axis) by the cells. As clearly can be seen, the proportion of cells which show a very strong reporter gene activity is significantly higher when the cells were cotransfected with a chromatin element capable of enhancing expression comprising a curved origin motif (nucleic acid sequence as shown in SEQ ID NO:3), and a vector comprising a modified neomycin phosphotransferase (nucleic acid sequence as shown in SEQ ID NO:13). Thus, the combined introduction of a modified neomycin phosphotransferase and chromatin element with an additional curved origin motif into CHO cells significantly enhances the expression of a cointroduced polynucleotide encoding for a product of interest (here a reporter gene).

In addition, a pEGFP-N1 vector comprising a modified NPT II gene described by Sautter and Enekel (mutant D227V, Sautter and Enekel, Biotechnology and Bioengineering, 89, (2005) 530-538) was cotransfected with DNA for AT rich region of the MII region of Intron 13 of the human topoisomerase I with an additional curved origin motif (SEQ ID NO:3) in CHO cells. Cells were cultivated, transfected with FuGENE 6 and selected with G418 medium as described in Example 3. After cultivation of 6 weeks in medium supplemented with 0.6 mg/ml G418 gene expression of individual cells was determined by FACS analysis as described in Example 3 (Instrument settings: gain of optical detector=200, amplification mode=4 decade logarithmic) (FIG. 7).

Although the described modified NPT II D227V mutant cotransfected with the AT rich region (SEQ ID NO:3) enhances the expression of the polynucleotide of interest relatively to the unmodified NPT gene cotransfected with the AT rich region (SEQ ID NO:3), the increase was less than for cointroducing a modified neomycin phosphotransferase of the present invention, e.g., having the nucleic acid sequence as shown in SEQ ID NO:16.

The invention claimed is:

1. A method for expressing at least one polynucleotide of interest, comprising:
   a) co-introducing into mammalian host cells
      (i) a first polynucleotide encoding a modified selectable marker gene having a reduced selection potential,
      (ii) a second polynucleotide comprising a first nucleic acid sequence for a Matrix Attachment Region (MAR) element which is capable of enhancing expression of at least one polynucleotide of interest, and at least one second nucleic acid sequence comprising a curved origin motif, and
      (iii) said at least one polynucleotide of interest encoding a polypeptide of interest; and
   b) cultivating said cells to express said at least one polynucleotide of interest,
   wherein said first polynucleotide encoding a modified selectable marker gene having a reduced selection potential is a polynucleotide encoding a modified neomycin phosphotransferase, and
   wherein said modified neomycin phosphotransferase has an amino acid substitution at A to G and T to S at positions 224 and 225 as compared to an unmodified neomycin phosphotransferase of SEQ ID NO: 35.

2. The method of claim 1, wherein said polynucleotide encoding a modified neomycin phosphotransferase is a polynucleotide comprising SEQ ID NO: 16 or encoding a polypeptide comprising SEQ ID NO: 13.

3. The method of claim 1, wherein the curved origin motif comprises SEQ ID NOs: 1, 2, 31 or 33, or at least two repeats of SEQ ID NO: 29, or at least two repeats of SEQ ID NO: 30, or at least two repeats of SEQ ID NO: 32 or at least two repeats of SEQ ID NO: 34.

4. The method of claim 1, wherein the curved origin motif comprises SEQ ID NO: 7, SEQ ID NO: 8, SEQ ID NO: 9, or SEQ ID NO: 10.

5. The method of claim 1, wherein the polynucleotide in (ii) comprises SEQ ID NO: 3, SEQ ID NO: 4, SEQ ID NO: 5, SEQ ID NO: 6, or a variant thereof being at least 80% identical to any one of SEQ ID NOs: 3, 4, 5 or 6 and comprising at least one curved origin motif.

6. The polynucleotide method of claim 1, wherein the polynucleotide in (ii) comprises SEQ ID NO: 3, or a variant thereof being at least 80% identical to SEQ ID NOs: 3 and comprising at least one curved origin motif.

7. The method of claim 1, wherein the host cell is cultivated in serum-free or serum-containing medium.

8. The method of claim 1, wherein the polypeptide of interest is selected from the group consisting of immunoglobulins, therapeutic proteins, membrane proteins and enzymes.

9. The method of claim 1, wherein step a) comprises co-introducing into said mammalian host cells
   (I) an expression vector comprising said first polynucleotide encoding a modified selectable marker gene having a reduced selection potential and said at least one polynucleotide of interest encoding a polypeptide of interest, and
   (II) a linear DNA fragment comprising said second polynucleotide comprising a first nucleic acid sequence for a Matrix Attachment Region (MAR) element which is capable of enhancing expression of said at least one polynucleotide of interest and at least one second nucleic acid sequence comprising a curved origin motif.

* * * * *

SEQUENCE LISTING

```
<160> NUMBER OF SEQ ID NOS: 75

<210> SEQ ID NO 1
<211> LENGTH: 28
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, c, g, or t
<220> FEATURE:
<221> NAME/KEY: misc_feature
<222> LOCATION: (18)..(22)
<223> OTHER INFORMATION: n is a, c, g, or t

<400> SEQUENCE: 1
attttannnn nattttannn nnatttta                                    28

<210> SEQ ID NO 2
<211> LENGTH: 28
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, c, g, or t
<220> FEATURE:
<221> NAME/KEY: misc_feature
<222> LOCATION: (18)..(22)
<223> OTHER INFORMATION: n is a, c, g, or t

<400> SEQUENCE: 2
taaaatnnnn ntaaaatnnn nntaaaat                                    28

<210> SEQ ID NO 3
<211> LENGTH: 3236
<212> TYPE: DNA
<213> ORGANISM: artificial
<220> FEATURE:
<223> OTHER INFORMATION: polynucleotide
```

<400> SEQUENCE: 3

```
ggatcccaat aggagtcatt aaaggcctgg aaaagtggtg ccattaggag aaaaagaaat     60
gatttcttga gcttgctctc agttctcttt taggctgtct tgtactcagc agaatagtga    120
gatcttcaaa ggttggggtt tgatagtgcc ttgaataatt tttaacttta tattgccagc    180
ggaagaagca ttctcttttt agatttaaaa aatgtagata caaatattag gggttttatt    240
tttagtgaaa catttcaaac atacaggaat agataattat gtaatgaaca ctcgtatgtc    300
caccatctgg ctttgtaaaa tcttaaaatt atgtcttatg tgctcaattg ttttatttca    360
taaaagatac tgataaacat agctgaagtc acttgtatac cattcacctt cttccctgta    420
gattactatg aactcggtct ttttattctc atacatattt tttgtatttt tgcagtatat    480
ttatgtgttc ataaacaata tgtaatttta caatatgtaa cacactagta acatactaat    540
ttaaaacttg tttttagttt acaatatgtt gtaaactatt gtaagctaaa gacatattgt    600
acaacctatt gttaaataaa aacaggtttt agtttttaaat taggtatgtt actgggatca    660
ttctgcaact tgtttattcc tctccagctt tgattttgtg gttttattat cttaacctac    720
acttttaatt aatccatttt atttgttaca tggtattcta ttatatcata aaaacttatc    780
tattctgttg gttttgttg ttggtcattt gagaccatgt cttcgctctg tcacccaggc    840
tggagtacag tggcgtgatc ttggctcact gtgacctctg cctcccggat tcaagtggtt    900
ttggtgcctc agcctcctga gtagctggga ttataggcgt gtgccaccat gcccagctaa    960
tttttgtatt tttaatagag acgggatttc accatgttgg ccaggctggt cttgaactga   1020
cctcaagtga tctgctcacc tcagctgcac aaagtgctgg gattacaggt gttagccaac   1080
caatacctg cctctattct cttgttaaga ggcatttagc atggttaata cagtctcttg   1140
ccctcataaa cagtgctggg aaggaaacac atgttcttgt gtatattgaa tgaaatttgt   1200
ttatacatta gatatttcca aatgttctct ttaagtactt cagtttacat cattactctc   1260
ctcctcccte ccctcccacc cccacccaca acagtattcc tcttttttcca tatccttgct   1320
aatgtttcaa agttttgctt tttacatttg ggtcttagat ccactagaat gtattttgc   1380
attgggatga agttgaaacc taatatattt tccaaatgag taaactgttg tcacagaact   1440
atttagttgt attacctcct ctcttgtata tcagatatat ctacatatat gtcagactgt   1500
ttctgggctg tctgtcctct ttaattagtt cgtgtatctg tttctgcatc agtagcatac   1560
tgtcttaact actgtagctt tataaagtct attgagtagg acaagtttgt ttcattcttc   1620
aaaattgctt tggctattct tggccctctg ctgtttcata ttaactttca gataaacttg   1680
tcaaattcta atgaaaactg ttgataaact tgttgattaa caaattctaa taaaaactgt   1740
tgagatttt attggaattg caatacattt atagattaac ggagaaagat attgacaata   1800
caattgagtt tccaattcac gaacatgtta tacctctcca ttaattcatg tcttttgaat   1860
gtatccacca atatggtttt gtaatttcct tcataaagga catttaaaat tcttatttta   1920
agtgatctta tagttttatg ctaacgtgaa tgagattttt ccattatgtt tctgttggtt   1980
attcctgaag tggtaatgct tataattttg gggtgttggt cttgtatctg cctaggagct   2040
cgattttagc tcgattttag ctcgatttta gctcgatttt agctcgattt tagctcgatt   2100
ttagctcgat tttagctcga ttttagctcg attttagctc gattttagct cgattttagc   2160
tcgattttag ctcgattttta gctcgatttt agctcgattt tagctcgatt ttagctcgat   2220
tttagctcga ttttagctcg attttagctc gattttagct cgattttagc tcgattttag   2280
```

```
ctcgactcga gcctaggaga tacaagaggt gctcagagtt gttcagggtt gctgaactct    2340
tagttctaaa agtgtctgtc atttggggtt tctatgtaga taatttaatt atctataaaa    2400
acagttcttc attttcagtt catatatttc atattttctt aagttttaat ttttattttt    2460
aaacacaatt atccataaac cctaacccct tccctagtca acagcagtca cagccaaatg    2520
ttttattaat tgctatactc agtgtttctt gtatctcata ccttctgggg tttcttgtct    2580
tgttgaaata caccctttaa tgtttcttta gtgaagaccc aacagtggca ctcactcacc    2640
tttgtttacc tgaaaatttc tttatttca tcttaattca tagtctgtct tttctccagt     2700
caaggaagtg tcttataggg aagattctgg tttcactatc gtgtatccag gatatatatg    2760
tatttataga tagacttttta atctgaggac taatgtattt tatcctacag tattaccaat    2820
cattatttct tccataactt ctagaccatt ccttttgtac ttctttttta gagtccttat    2880
tagatgagtg ttgactcttt tcaatctaga catctttttt aaactatatt ttcatactct    2940
ttgtctcttt aggtctgatt ttttaagttc aggggatatt tcattttggg tgagttgtag    3000
cactacttca attcactaat tctaattata tttaatctac aagttattcc atctataatt    3060
tatttcaatt accactttt gttttcaaaa tttctaattt tatatctgat tttgtttcat     3120
ttttgtttta taatttcatg ttcttctag atttacatc ttttatgca tactaaacat       3180
actcacttga aagtctttgt aagattgttc tataaaatgt tacctgaagt gaattc        3236
```

<210> SEQ ID NO 4
<211> LENGTH: 3236
<212> TYPE: DNA
<213> ORGANISM: artificial
<220> FEATURE:
<223> OTHER INFORMATION: polynucleotide

<400> SEQUENCE: 4

```
ggatcccaat aggagtcatt aaaggcctgg aaaagtggtg ccattaggag aaaaagaaat      60
gatttcttga gcttgctctc agttctcttt taggctgtct tgtactcagc agaatagtga    120
gatcttcaaa ggttggggtt tgatagtgcc ttgaataatt tttaacttta tattgccagc    180
ggaagaagca ttctcttttt agatttaaaa aatgtagata caaatattag gggttttatt    240
tttagtgaaa catttcaaac atacaggaat agataattat gtaatgaaca ctcgtatgtc    300
caccatctgg ctttgtaaaa tcttaaaatt atgtcttatg tgctcaattg tttttatttca   360
taaaagatac tgataaacat agctgaagtc acttgtatac cattcacctt cttccctgta    420
gattactatg aactcggtct ttttattctc atacatattt tttgtatttt tgcagtatat    480
ttatgtgttc ataaacaata tgtaattta caatatgtaa cacactagta acatactaat     540
ttaaaacttg tttttagttt acaatatgtt gtaaactatt gtaagctaaa gacatattgt    600
acaacctatt gttaaataaa acaggttttt agttttaaat taggtatgtt actgggatca    660
ttctgcaact tgtttattcc tctccagctt tgatttgtg gttttattat cttaacctac      720
acttttaatt aatccatttt atttgttaca tggtattcta ttatatcata aaaacttatc    780
tattctgttg gtttttgttg ttggtcattt gagaccatgt cttcgctctg tcacccaggc    840
tggagtacag tggcgtgatc ttggctcact gtgacctctg cctcccggat tcaagtggtt    900
ttggtgcctc agcctcctga gtagctggga ttataggcgt gtgccaccat gcccagctaa    960
ttttttgtatt tttaatagag acgggatttc accatgttgg ccaggctggt cttgaactga   1020
cctcaagtga tctgctcacc tcagctgcac aaagtgctgg gattacaggt gttagccaac    1080
caatacctg cctctattct cttgttaaga ggcatttagc atggttaata cagtctcttg     1140
```

```
ccctcataaa cagtgctggg aaggaaacac atgttcttgt gtatattgaa tgaaatttgt    1200
ttatacatta gatatttcca aatgttctct ttaagtactt cagtttacat cattactctc    1260
ctcctccctc ccctcccacc cccacccaca acagtattcc tcttttttcca tatccttgct    1320 aatgtttcaa agttttgctt tttacatttg ggtcttagat ccactagaat gtattttttgc   1380 attgggatga agttgaaacc taatatattt tccaaatgag taaactgttg tcacagaact    1440
atttagttgt attacctcct ctcttgtata tcagatatat ctacatatat gtcagactgt    1500
ttctgggctg tctgtcctct ttaattagtt cgtgtatctg tttctgcatc agtagcatac    1560
tgtcttaact actgtagctt tataaagtct attgagtagg acaagtttgt ttcattcttc    1620
aaaattgctt tggctattct tggccctctg ctgtttcata ttaactttca gataaacttg    1680
tcaaattcta atgaaaactg ttgataaact tgttgattaa caaattctaa taaaaactgt    1740
tgagattttt attggaattg caatacattt atagattaac ggagaaagat attgacaata    1800
caattgagtt tccaattcac gaacatgtta tacctctcca ttaattcatg tcttttgaat    1860
gtatccacca atatggtttt gtaattttct tcataaagga catttaaaat tcttatttta    1920
agtgatctta tagtttttatg ctaacgtgaa tgagattttt ccattatgtt tctgttggtt    1980
attcctgaag tggtaatgct tataatttttg gggtgttggt cttgtatctg cctaggctcg    2040
agtcgagcta aaatcgagct aaaatcgagc taaaatcgag ctaaaatcga gctaaaatcg    2100
agctaaaatc gagctaaaat cgagctaaaa tcgagctaaa atcgagctaa aatcgagcta    2160
aaatcgagct aaaatcgagc taaaatcgag ctaaaatcga gctaaaatcg agctaaaatc    2220
gagctaaaat cgagctaaaa tcgagctaaa atcgagctaa aatcgagcta aaatcgagct    2280
aaaatcgagc tcctaggaga tacaagaggt gctcagagtt gttcagggtt gctgaactct    2340
tagttctaaa agtgtctgtc atttggggtt tctatgtaga taatttaatt atctataaaa    2400
acagttcttc attttcagtt catatatttc atattttctt aagttttaat ttttattttt    2460
aaacacaatt atccataaac cctaacccctt tccctagtca acagcagtca cagccaaatg    2520
ttttattaat tgctatactc agtgtttctt gtatctcata ccttctgggg tttcttgtct    2580
tgttgaaata caccctttaa tgtttcttta gtgaagaccc aacagtggca ctcactcacc    2640 tttgttacc tgaaaatttc tttattttca tcttaattca tagtctgtct tttctccagt     2700
caaggaagtg tcttataggg aagattctgg tttcactatc gtgtatccag gatatatatg    2760
tatttataga tagacttttta atctgaggac taatgtattt tatcctacag tattaccaat    2820
cattatttct tccataactt ctagaccatt ccttttgtac ttcttttttta gagtccttat    2880 tagatgagtg ttgactcttt tcaatctaga catcttttt aaactatatt ttcatactct     2940
ttgtctcttt aggtctgatt ttttaagttc aggggatatt tcattttggg tgagttgtag    3000
cactacttca attcactaat tctaattata tttaatctac aagttattcc atctataatt    3060
tatttcaatt accacttttt gttttcaaaa tttctaattt tatatctgat tttgtttcat    3120
ttttgtttta taatttcatg ttctttctag attttacatc ttttttatgca tactaaacat    3180 actcacttga aagtctttgt aagattgttc tataaaatgt tacctgaagt gaattc        3236
```

<210> SEQ ID NO 5
<211> LENGTH: 3249
<212> TYPE: DNA
<213> ORGANISM: artificial
<220> FEATURE:
<223> OTHER INFORMATION: polynucleotide -continued

```
<400> SEQUENCE: 5
ggatcccaat aggagtcatt aaaggcctgg aaaagtggtg ccattaggag aaaaagaaat      60
gatttcttga gcttgctctc agttctcttt taggctgtct tgtactcagc agaatagtga     120
gatcttcaaa ggttggggtt tgatagtgcc ttgaataatt tttaacttta tattgccagc     180
ggaagaagca ttctcttttt agatttaaaa aatgtagata caaatattag gggttttatt     240
tttagtgaaa catttcaaac atacaggaat agataattat gtaatgaaca ctcgtatgtc     300
caccatctgg ctttgtaaaa tcttaaaatt atgtcttatg tgctcaattg ttttatttca     360
taaaagatac tgataaacat agctgaagtc acttgtatac cattcacctt cttccctgta     420
gattactatg aactcggtct ttttattctc atacatattt tttgtatttt tgcagtatat     480
ttatgtgttc ataaacaata tgtaattttta caatatgtaa cacactagta acatactaat     540
ttaaaacttg tttttagttt acaatatgtt gtaaactatt gtaagctaaa gacatattgt     600
acaacctatt gtaaaataaa acaggtttt agttttaaat taggtatgtt actgggatca      660
ttctgcaact tgtttattcc tctccagctt tgattttgtg gttttattat cttaacctac     720
acttttaatt aatccatttt atttgttaca tggtattcta ttatatcata aaaacttatc     780
tattctgttg gttttgttg ttggtcattt gagaccatgt cttcgctctg tcacccaggc      840
tggagtacag tggcgtgatc ttggctcact gtgacctctg cctcccggat tcaagtggtt     900
ttggtgcctc agcctcctga gtagctggga ttataggcgt gtgccaccat gcccagctaa     960 ttttttgtatt tttaatagag acgggatttc accatgttgg ccaggctggt cttgaactga    1020
cctcaagtga tctgctcacc tcagctgcac aaagtgctgg gattacaggt gttagccacc    1080
ataccctgcc tctattctct tgttaagagg catttagcat ggttatacag tctcttgccc    1140
tcataaacag tgctggaaga aacacatgtt tcttgtgtat atgaatgaaa atttgtttta    1200
tacattagat atttccaaat tgttctctta agtacttcag tttacatcat tactctcctc    1260
ctccctcccc tcccacccccc acccacaaca gtattcctct ttttccatat ccttgctaat    1320
gtttctaaag ttttgctttt tacatttggg tcttagatcc actagaatgt attttttgcat    1380 tgggatgaag ttgaaaccta atatattttc caaatgagta aactgttgtc acagaactat    1440
ttagttgtat tacctcctct cttgtatatc agatatatct acatatatgt cagactgttt    1500
ctgggctgtc tgtcctcttt aattagttcg tgtatctgtt tctgcatcag tagcatactg    1560
tcttaactac tgtagcttta taaagtctat tgagtaggac aagtttgttt cattcttcaa    1620
aattgctttg gctattcttg gccctctgct gtttcatatt aactttcaga taaacttgtc    1680
aaattctaat gaaaactgtt gataaacttg ttgattaaca aattctaata aaaactgttg    1740 agattttttat tggaattgca atacattta agattaacgg agaaagatat tgacaataca    1800
attgagtttc caattcacga acatgttata cctctccatt aattcatgtc ttttgaatgt    1860
atccaccaat atggttttgt aatttttcttc ataaaggttt tacatttaaa aaattccttat    1920 ttttaagtga tcttatagtt tttattgcta atgtgaatga attttttttc cattatgttt    1980
ctgttggtta ttcctgaagt ggtaatgctt ataattttgg ggtgttggtc ttgtatctgc    2040
ctaggagctc gatttagct cgattttagc tcgattttag ctcgatttta gctcgatttt    2100
agctcgattt tagctcgatt ttagctcgat tttagctcga ttttagctcg attttagctc    2160
gattttagct cgattttagc tcgattttag ctcgatttta gctcgatttt agctcgattt    2220
tagctcgatt ttagctcgat tttagctcga ttttagctcg attttagctc gattttagct    2280
cgattttagc tcgactcgag cctaggagat acaagaggtg ctcagagttg ttcagggttg    2340
```

```
ctgaactctt agttctaaaa gtgtctgtca tttggggttt ctatgtgat  aatttaatta    2400 tctataaaaa cagttcttca ttttcagttc atatatttca tatttcttta agttttaatt    2460
tttattttta aacacaatta tccataaaaac cctaacccct tccctagtca acagcagtca   2520
cagccaaatg ttttattaat tgctatactc agtgttctt gtatctcata ccttctgggg     2580
tttcttgtct tgttgaaata caccctttaa tgtttcttta gtgaagaccc aacagtggca    2640
ctcactcacc tttgtttacc tgaaaatttc tttattttca tcttaattca tagtctgtct    2700
tttctccagt caaggaagtg tcttataggg aagattctgg tttcactatg ctgtatccag    2760
ggatatatat gtatttatag atagactttt aatctgagga ctaatgtatt ttatcctaca    2820
gtattaccaa tcattatttc ttccataact tctagaccat tcctttttgta cttcttttttt   2880 agagtccctat tagatgagtg ttgacactttt tcaatctaga catctttttt aaactatatt   2940
ttcatactct ttgtctcttt aggtctgatt ttttaagttc aggggaatat ttcattttgg    3000
gtgagttgta gcactcactt ccaattcact aattctaatt atatttaatc tacaagttat    3060
tccatctata atttatttca attaccactt tttgttttca aaatttctaa ttttatatct    3120
gattttgttt cattttttgtt ttataatttc atgttcttc tagattttac atctttttat    3180
gcatactaaa catactcact tgaaagtctt tgtaagattg ttctataaaa tgttacctga    3240
agtgaattc                                                             3249

<210> SEQ ID NO 6
<211> LENGTH: 3249
<212> TYPE: DNA
<213> ORGANISM: artificial
<220> FEATURE:
<223> OTHER INFORMATION: polynucleotide

<400> SEQUENCE: 6
ggatcccaat aggagtcatt aaaggcctgg aaaagtggtg ccattaggag aaaaagaaat       60
gatttcttga gcttgctctc agttctcttt taggctgtct tgtactcagc agaatagtga     120
gatcttcaaa ggttggggtt tgatagtgcc ttgaataatt tttaacttta tattgccagc     180
ggaagaagca ttctcttttt agatttaaaa aatgtagata caaatattag gggttttatt    240
tttagtgaaa catttcaaac atacaggaat agataattat gtaatgaaca ctcgtatgtc    300
caccatctgg ctttgtaaaa tcttaaaatt atgtcttatg tgctcaattg ttttatttca    360
taaaagatac tgataaacat agctgaagtc acttgtatac cattcacctt cttccctgta    420
gattactatg aactcggtct ttttattctc atacatattt tttgtatttt tgcagtatat    480
ttatgtgttc ataaacaata tgtaattta caatatgtaa cacactagta acatactaat    540
ttaaaacttg tttttagttt acaatatgtt gtaaactatt gtaagctaaa gacatattgt    600
acaacctatt gtaaaataaa aacaggtttt agttttaaat taggtatgtt actgggatca    660
ttctgcaact tgtttattcc tctccagctt tgattttgtg gttttattat cttaacctac    720 actttttaatt aatccatttt atttgttaca tggtattcta ttatatcata aaaacttatc    780
tattctgttg gttttgttg ttggtcattt gagaccatgt cttcgctctg tcacccaggc     840
tggagtacag tggcgtgatc ttggctcact gtgacctctg cctcccggat tcaagtggtt    900
ttggtgcctc agcctcctga gtagctggga ttataggcgt gtgccaccat gcccagctaa    960
tttttgtatt tttaatagag acgggatttc accatgttgg ccaggctggt cttgaactga   1020
cctcaagtga tctgctcacc tcagctgcac aaagtgctgg gattacaggt gttagccacc    1080
```

```
ataccctgcc tctattctct tgttaagagg catttagcat ggttatacag tctcttgccc    1140
tcataaacag tgctggaaga aacacatgtt tcttgtgtat atgaatgaaa atttgtttta    1200
tacattagat atttccaaat tgttctctta agtacttcag tttacatcat tactctcctc    1260
ctccctcccc tcccaccccc acccacaaca gtattcctct ttttccatat ccttgctaat    1320
gtttctaaag ttttgctttt tacatttggg tcttagatcc actagaatgt attttgcat    1380 tgggatgaag ttgaaaccta atatattttc caaatgagta aactgttgtc acagaactat    1440
ttagttgtat tacctcctct cttgtatatc agatatatct acatatatgt cagactgttt    1500
ctgggctgtc tgtcctcttt aattagttcg tgtatctgtt tctgcatcag tagcatactg    1560
tcttaactac tgtagcttta taaagtctat tgagtaggac aagtttgttt cattcttcaa    1620
aattgctttg ctattcttg gccctctgct gtttcatatt aactttcaga taaacttgtc     1680
aaattctaat gaaaactgtt gataaacttg ttgattaaca aattctaata aaaactgttg    1740
agatttttat tggaattgca atacatttat agattaacgg agaaagatat tgacaataca    1800
attgagtttc caattcacga acatgttata cctctccatt aattcatgtc ttttgaatgt    1860
atccaccaat atggttttgt aatttcttc ataaaggttt tacatttaaa aaattcttat     1920
ttttaagtga tcttatagtt tttattgcta atgtgaatga attttttc cattatgttt      1980 ctgttggtta ttcctgaagt ggtaatgctt ataattttgg ggtgttggtc ttgtatctgc    2040
ctaggctcga gtcgagctaa aatcgagcta aaatcgagct aaaatcgagc taaaatcgag    2100
ctaaaatcga gctaaaatcg agctaaaatc gagctaaaat cgagctaaaa tcgagctaaa    2160
atcgagctaa aatcgagcta aaatcgagct aaaatcgagc taaaatcgag ctaaaatcga    2220
gctaaaatcg agctaaaatc gagctaaaat cgagctaaaa tcgagctaaa atcgagctaa    2280
aatcgagcta aaatcgagct cctaggagat acaagaggtg ctcagagttg ttcagggttg    2340
ctgaactctt agttctaaaa gtgtctgtca tttggggttt ctatgtagat aatttaatta    2400
tctataaaaa cagttcttca ttttcagttc atatatttca tatttcttta agttttaatt    2460
tttattttta aacacaatta tccataaaac cctaaccctt tccctagtca acagcagtca    2520
cagccaaatg ttttattaat tgctatactc agtgtttctt gtatctcata ccttctgggg    2580
tttcttgtct tgttgaaata cacccttaa tgtttcttta gtgaagaccc aacagtggca     2640
ctcactcacc tttgtttacc tgaaaatttc tttattttca tcttaattca tagtctgtct    2700
tttctccagt caaggaagtg tcttataggg aagattctgg tttcactatg ctgtatccag    2760
ggatatatat gtatttatag atagactttt aatctgagga ctaatgtatt ttatcctaca    2820
gtattaccaa tcattatttc ttccataact tctagaccat tccttttgta cttctttttt    2880
agagtcctat tagatgagtg ttgacacttt tcaatctaga catctttttt aaactatatt    2940
ttcatactct ttgtctcttt aggtctgatt ttttaagttc aggggaatat ttcattttgg    3000
gtgagttgta gcactcactt ccaattcact aattctaatt atatttaatc tacaagttat    3060
tccatctata atttatttca attaccactt tttgttttca aaatttctaa ttttatatct    3120
gattttgttt cattttttgtt ttataatttc atgttctttc tagattttac atctttttat   3180
gcatactaaa catactcact tgaaagtctt tgtaagattg ttctataaaa tgttacctga    3240
agtgaattc                                                            3249
```

<210> SEQ ID NO 7
<211> LENGTH: 237
<212> TYPE: DNA
<213> ORGANISM: artificial

```
<220> FEATURE:
<223> OTHER INFORMATION: polynucleotide

<400> SEQUENCE: 7
attttagctc gattttagct cgattttagc tcgattttag ctcgatttta gctcgatttt      60
agctcgattt tagctcgatt ttagctcgat tttagctcga ttttagctcg attttagctc     120
gattttagct cgattttagc tcgattttag ctcgatttta gctcgatttt agctcgattt     180
tagctcgatt ttagctcgat tttagctcga ttttagctcg attttagctc gatttta        237

<210> SEQ ID NO 8
<211> LENGTH: 237
<212> TYPE: DNA
<213> ORGANISM: artificial
<220> FEATURE:
<223> OTHER INFORMATION: polynucleotide

<400> SEQUENCE: 8
taaaatcgag ctaaaatcga gctaaaatcg agctaaaatc gagctaaaat cgagctaaaa      60
tcgagctaaa atcgagctaa aatcgagcta aaatcgagct aaaatcgagc taaaatcgag     120
ctaaaatcga gctaaaatcg agctaaaatc gagctaaaat cgagctaaaa tcgagctaaa     180
atcgagctaa aatcgagcta aaatcgagct aaaatcgagc taaaatcgag ctaaaat        237

<210> SEQ ID NO 9
<211> LENGTH: 237
<212> TYPE: DNA
<213> ORGANISM: artificial
<220> FEATURE:
<223> OTHER INFORMATION: polynucleotide
<220> FEATURE:
<221> NAME/KEY: misc_feature
<222> LOCATION: (7)..(11)
<223> OTHER INFORMATION: n is a, c, g, or t
<220> FEATURE:
<221> NAME/KEY: misc_feature
<222> LOCATION: (18)..(22)
<223> OTHER INFORMATION: n is a, c, g, or t
<220> FEATURE:
<221> NAME/KEY: misc_feature
<222> LOCATION: (29)..(33)
<223> OTHER INFORMATION: n is a, c, g, or t
<220> FEATURE:
<221> NAME/KEY: misc_feature
<222> LOCATION: (40)..(44)
<223> OTHER INFORMATION: n is a, c, g, or t
<220> FEATURE:
<221> NAME/KEY: misc_feature
<222> LOCATION: (51)..(55)
<223> OTHER INFORMATION: n is a, c, g, or t
<220> FEATURE:
<221> NAME/KEY: misc_feature
<222> LOCATION: (62)..(66)
<223> OTHER INFORMATION: n is a, c, g, or t
<220> FEATURE:
<221> NAME/KEY: misc_feature
<222> LOCATION: (73)..(77)
<223> OTHER INFORMATION: n is a, c, g, or t
<220> FEATURE:
<221> NAME/KEY: misc_feature
<222> LOCATION: (84)..(88)
<223> OTHER INFORMATION: n is a, c, g, or t
<220> FEATURE:
<221> NAME/KEY: misc_feature
<222> LOCATION: (95)..(99)
<223> OTHER INFORMATION: n is a, c, g, or t
<220> FEATURE:
<221> NAME/KEY: misc_feature
<222> LOCATION: (106)..(110)
<223> OTHER INFORMATION: n is a, c, g, or t
<220> FEATURE:
```

```
<221> NAME/KEY: misc_feature
<222> LOCATION: (117)..(121)
<223> OTHER INFORMATION: n is a, c, g, or t
<220> FEATURE:
<221> NAME/KEY: misc_feature
<222> LOCATION: (128)..(132)
<223> OTHER INFORMATION: n is a, c, g, or t
<220> FEATURE:
<221> NAME/KEY: misc_feature
<222> LOCATION: (139)..(143)
<223> OTHER INFORMATION: n is a, c, g, or t
<220> FEATURE:
<221> NAME/KEY: misc_feature
<222> LOCATION: (150)..(154)
<223> OTHER INFORMATION: n is a, c, g, or t
<220> FEATURE:
<221> NAME/KEY: misc_feature
<222> LOCATION: (161)..(165)
<223> OTHER INFORMATION: n is a, c, g, or t
<220> FEATURE:
<221> NAME/KEY: misc_feature
<222> LOCATION: (172)..(176)
<223> OTHER INFORMATION: n is a, c, g, or t
<220> FEATURE:
<221> NAME/KEY: misc_feature
<222> LOCATION: (183)..(187)
<223> OTHER INFORMATION: n is a, c, g, or t
<220> FEATURE:
<221> NAME/KEY: misc_feature
<222> LOCATION: (194)..(198)
<223> OTHER INFORMATION: n is a, c, g, or t
<220> FEATURE:
<221> NAME/KEY: misc_feature
<222> LOCATION: (205)..(209)
<223> OTHER INFORMATION: n is a, c, g, or t
<220> FEATURE:
<221> NAME/KEY: misc_feature
<222> LOCATION: (216)..(220)
<223> OTHER INFORMATION: n is a, c, g, or t
<220> FEATURE:
<221> NAME/KEY: misc_feature
<222> LOCATION: (227)..(231)
<223> OTHER INFORMATION: n is a, c, g, or t

<400> SEQUENCE: 9
attttannnn nattttann nnattttann nnnattttan nnnnatttta nnnnnatttt      60
annnnnattt tannnnnatt ttannnnnat tttannnnna ttttannnnn attttannnn     120
nattttannn nnattttann nnnattttan nnnnatttta nnnnnatttt annnnnattt     180
tannnnnatt ttannnnnat tttannnnna ttttannnnn attttannnn natttta       237

<210> SEQ ID NO 10
<211> LENGTH: 237
<212> TYPE: DNA
<213> ORGANISM: artificial
<220> FEATURE:
<223> OTHER INFORMATION: polynucleotide
<220> FEATURE:
<221> NAME/KEY: misc_feature
<222> LOCATION: (7)..(11)
<223> OTHER INFORMATION: n is a, c, g, or t
<220> FEATURE:
<221> NAME/KEY: misc_feature
<222> LOCATION: (18)..(22)
<223> OTHER INFORMATION: n is a, c, g, or t
<220> FEATURE:
<221> NAME/KEY: misc_feature
<222> LOCATION: (29)..(33)
<223> OTHER INFORMATION: n is a, c, g, or t
<220> FEATURE:
<221> NAME/KEY: misc_feature
<222> LOCATION: (40)..(44)
<223> OTHER INFORMATION: n is a, c, g, or t
<220> FEATURE:
<221> NAME/KEY: misc_feature
```

<220> FEATURE:
<221> NAME/KEY: misc_feature
<222> LOCATION: (51)..(55)
<223> OTHER INFORMATION: n is a, c, g, or t
<220> FEATURE:
<221> NAME/KEY: misc_feature
<222> LOCATION: (62)..(66)
<223> OTHER INFORMATION: n is a, c, g, or t
<220> FEATURE:
<221> NAME/KEY: misc_feature
<222> LOCATION: (73)..(77)
<223> OTHER INFORMATION: n is a, c, g, or t
<220> FEATURE:
<221> NAME/KEY: misc_feature
<222> LOCATION: (84)..(88)
<223> OTHER INFORMATION: n is a, c, g, or t
<220> FEATURE:
<221> NAME/KEY: misc_feature
<222> LOCATION: (95)..(99)
<223> OTHER INFORMATION: n is a, c, g, or t
<220> FEATURE:
<221> NAME/KEY: misc_feature
<222> LOCATION: (106)..(110)
<223> OTHER INFORMATION: n is a, c, g, or t
<220> FEATURE:
<221> NAME/KEY: misc_feature
<222> LOCATION: (117)..(121)
<223> OTHER INFORMATION: n is a, c, g, or t
<220> FEATURE:
<221> NAME/KEY: misc_feature
<222> LOCATION: (128)..(132)
<223> OTHER INFORMATION: n is a, c, g, or t
<220> FEATURE:
<221> NAME/KEY: misc_feature
<222> LOCATION: (139)..(143)
<223> OTHER INFORMATION: n is a, c, g, or t
<220> FEATURE:
<221> NAME/KEY: misc_feature
<222> LOCATION: (150)..(154)
<223> OTHER INFORMATION: n is a, c, g, or t
<220> FEATURE:
<221> NAME/KEY: misc_feature
<222> LOCATION: (161)..(165)
<223> OTHER INFORMATION: n is a, c, g, or t
<220> FEATURE:
<221> NAME/KEY: misc_feature
<222> LOCATION: (172)..(176)
<223> OTHER INFORMATION: n is a, c, g, or t
<220> FEATURE:
<221> NAME/KEY: misc_feature
<222> LOCATION: (183)..(187)
<223> OTHER INFORMATION: n is a, c, g, or t
<220> FEATURE:
<221> NAME/KEY: misc_feature
<222> LOCATION: (194)..(198)
<223> OTHER INFORMATION: n is a, c, g, or t
<220> FEATURE:
<221> NAME/KEY: misc_feature
<222> LOCATION: (205)..(209)
<223> OTHER INFORMATION: n is a, c, g, or t
<220> FEATURE:
<221> NAME/KEY: misc_feature
<222> LOCATION: (216)..(220)
<223> OTHER INFORMATION: n is a, c, g, or t
<220> FEATURE:
<221> NAME/KEY: misc_feature
<222> LOCATION: (227)..(231)
<223> OTHER INFORMATION: n is a, c, g, or t

<400> SEQUENCE: 10
taaaatnnnn ntaaaatnnn nntaaaatnn nnntaaaatn nnnntaaaat nnnnntaaaa    60
tnnnnntaaa atnnnnntaa aatnnnnnta aaatnnnnnt aaaatnnnnn taaaatnnnn   120
ntaaaatnnn nntaaaatnn nnntaaaatn nnnntaaaat nnnnntaaaa tnnnnntaaa   180
atnnnnntaa aatnnnnnta aaatnnnnnt aaaatnnnnn taaaatnnnn ntaaaat      237

<210> SEQ ID NO 11

<211> LENGTH: 264
<212> TYPE: PRT
<213> ORGANISM: artificial
<220> FEATURE:
<223> OTHER INFORMATION: polypeptide

<400> SEQUENCE: 11

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Ala Asp Ile Ala Glu Glu Leu Gly Gly Glu Trp Ala Asp Arg Phe
225                 230                 235                 240

Leu Val Leu Tyr Gly Ile Ala Pro Asp Ser Gln Arg Ile Ala Phe
                245                 250                 255

Tyr Arg Leu Leu Asp Glu Phe Phe
            260
```

<210> SEQ ID NO 12
<211> LENGTH: 264
<212> TYPE: PRT
<213> ORGANISM: artificial
<220> FEATURE:
<223> OTHER INFORMATION: polypeptide

<400> SEQUENCE: 12

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
```

-continued

```
                50                  55                  60
Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Gly Glu
                 85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Val Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 13
<211> LENGTH: 264
<212> TYPE: PRT
<213> ORGANISM: artificial
<220> FEATURE:
<223> OTHER INFORMATION: polypeptide

<400> SEQUENCE: 13

Met Ile Glu Gln Asp Gly Leu His Ala Gly Ser Pro Ala Ala Trp Val
 1               5                  10                  15

Glu Arg Leu Phe Gly Tyr Asp Trp Ala Gln Gln Thr Ile Gly Cys Ser
                 20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
        50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Gly Glu
                 85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Asp Leu Asp Glu
```

```
                   145                 150                 155                 160
Glu His Gln Gly Leu Ala Pro Ala Glu Leu Phe Ala Arg Leu Lys Ala
                165                 170                 175
Ser Met Pro Asp Gly Glu Asp Leu Val Val Thr His Gly Asp Ala Cys
            180                 185                 190
Leu Pro Asn Ile Met Val Glu Asn Gly Arg Phe Ser Gly Phe Ile Asp
        195                 200                 205
Cys Gly Arg Leu Gly Val Ala Asp Arg Tyr Gln Asp Ile Ala Leu Gly
    210                 215                 220
Ser Arg Asp Ile Ala Glu Glu Leu Gly Gly Glu Trp Ala Asp Arg Phe
225                 230                 235                 240
Leu Val Leu Tyr Gly Ile Ala Ala Pro Asp Ser Gln Arg Ile Ala Phe
                245                 250                 255
Tyr Arg Leu Leu Asp Glu Phe Phe
                260

<210> SEQ ID NO 14
<211> LENGTH: 795
<212> TYPE: DNA
<213> ORGANISM: artificial
<220> FEATURE:
<223> OTHER INFORMATION: polynucleotide

<400> SEQUENCE: 14
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caagacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgag catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctaccgctga tatcgctgaa gagcttggcg gcgaatgggc tgaccgcttc     720
ctcgtgcttt acggtatcgc cgctcccgat tcgcagcgca tcgccttcta tcgccttctt     780
gacgagttct tctga                                                      795

<210> SEQ ID NO 15
<211> LENGTH: 795
<212> TYPE: DNA
<213> ORGANISM: artificial
<220> FEATURE:
<223> OTHER INFORMATION: polynucleotide

<400> SEQUENCE: 15
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caagacgagg cagcgcggct atcgtggctg gccacgacgg gcgttccttg cgcagctgtg     240
```

```
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgag catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctaccgttga tatcgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795

<210> SEQ ID NO 16
<211> LENGTH: 795
<212> TYPE: DNA
<213> ORGANISM: artificial
<220> FEATURE:
<223> OTHER INFORMATION: polynucleotide

<400> SEQUENCE: 16
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caagacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgag catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg gatcccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795

<210> SEQ ID NO 17
<211> LENGTH: 795
<212> TYPE: DNA
<213> ORGANISM: Escherichia coli

<400> SEQUENCE: 17
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caagacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
```

```
atcgagcgag cacgtactcg gatggaagcc ggtcttgtcg atcaggatga tctggacgaa    480
gagcatcagg ggctcgcgcc agccgaactg ttcgccaggc tcaaggcgag catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795
```

```
<210> SEQ ID NO 18
<211> LENGTH: 25
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (5)..(11)
<223> OTHER INFORMATION: n is a, c, g, or t
<220> FEATURE:
<221> NAME/KEY: misc_feature
<222> LOCATION: (15)..(21)
<223> OTHER INFORMATION: n is a, c, g, or t

<400> SEQUENCE: 18 aaaannnnn naaannnnnn naaaa                                            25
```

```
<210> SEQ ID NO 19
<211> LENGTH: 26
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (5)..(11)
<223> OTHER INFORMATION: n is a, c, g, or t
<220> FEATURE:
<221> NAME/KEY: misc_feature
<222> LOCATION: (16)..(22)
<223> OTHER INFORMATION: n is a, c, g, or t

<400> SEQUENCE: 19
aaaannnnnn naaaannnnn nnaaaa                                          26
```

```
<210> SEQ ID NO 20
<211> LENGTH: 25
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (5)..(11)
<223> OTHER INFORMATION: n is a, c, g, or t
<220> FEATURE:
<221> NAME/KEY: misc_feature
<222> LOCATION: (15)..(21)
<223> OTHER INFORMATION: n is a, c, g, or t

<400> SEQUENCE: 20
ttttnnnnnn ntttnnnnnn ntttt                                           25
```

```
<210> SEQ ID NO 21
<211> LENGTH: 26
<212> TYPE: DNA
```

```
<213> ORGANISM: artificial
<220> FEATURE:
<223> OTHER INFORMATION: oligonucleotide
<220> FEATURE:
<221> NAME/KEY: misc_feature
<222> LOCATION: (5)..(11)
<223> OTHER INFORMATION: n is a, c, g, or t
<220> FEATURE:
<221> NAME/KEY: misc_feature
<222> LOCATION: (16)..(22)
<223> OTHER INFORMATION: n is a, c, g, or t

<400> SEQUENCE: 21 ttttnnnnn nttttnnnnn nntttt                                  26

<210> SEQ ID NO 22
<211> LENGTH: 6
<212> TYPE: DNA
<213> ORGANISM: artificial
<220> FEATURE:
<223> OTHER INFORMATION: oligonucleotide

<400> SEQUENCE: 22 tttaaa                                                        6

<210> SEQ ID NO 23
<211> LENGTH: 6
<212> TYPE: DNA
<213> ORGANISM: artificial
<220> FEATURE:
<223> OTHER INFORMATION: oligonucleotide

<400> SEQUENCE: 23 aaattt                                                        6

<210> SEQ ID NO 24
<211> LENGTH: 4
<212> TYPE: DNA
<213> ORGANISM: artificial
<220> FEATURE:
<223> OTHER INFORMATION: oligonucleotide

<400> SEQUENCE: 24 atta                                                          4

<210> SEQ ID NO 25
<211> LENGTH: 5
<212> TYPE: DNA
<213> ORGANISM: artificial
<220> FEATURE:
<223> OTHER INFORMATION: oligonucleotide

<400> SEQUENCE: 25 attta                                                         5

<210> SEQ ID NO 26
<211> LENGTH: 6
<212> TYPE: DNA
<213> ORGANISM: artificial
<220> FEATURE:
<223> OTHER INFORMATION: oligonucleotide

<400> SEQUENCE: 26 atttta                                                        6

<210> SEQ ID NO 27
<211> LENGTH: 2974
```

<212> TYPE: DNA
<213> ORGANISM: Homo sapiens

<400> SEQUENCE: 27

```
ggatcccaat aggagtcatt aaaggcctgg aaaagtggtg ccattaggag aaaaagaaat        60
gatttcttga gcttgctctc agttctcttt taggctgtct tgtactcagc agaatagtga       120
gatcttcaaa ggttggggtt tgatagtgcc ttgaataatt tttaacttta tattgccagc       180
ggaagaagca ttctcttttt agatttaaaa aatgtagata caaatattag gggttttatt       240
tttagtgaaa catttcaaac atacaggaat agataattat gtaatgaaca ctcgtatgtc       300
caccatctgg ctttgtaaaa tcttaaaatt atgtcttatg tgctcaattg ttttatttca       360
taaaagatac tgataaacat agctgaagtc acttgtatac cattcacctt cttccctgta       420
gattactatg aactcggtct ttttattctc atacatattt tttgtatttt tgcagtatat       480
ttatgtgttc ataaacaata tgtaatttta caatatgtaa cacactagta acatactaat       540
ttaaaacttg tttttagttt acaatatgtt gtaaactatt gtaagctaaa gacatattgt       600
acaacctatt gttaaataaa aacaggtttt agttttaaat taggtatgtt actgggatca       660
ttctgcaact tgtttattcc tctccagctt tgattttgtg gttttattat cttaacctac       720
actttaattt aatccatttt atttgttaca tggtattcta ttatatcata aaaacttatc       780
tattctgttg gttttgttg ttggtcattt gagaccatgt cttcgctctg tcacccaggc       840
tggagtacag tggcgtgatc ttggctcact gtgacctctg cctcccggat tcaagtggtt       900
ttggtgcctc agcctcctga gtagctggga ttataggcgt gtgccaccat gcccagctaa       960
ttttgtatt tttaatagag acgggatttc accatgttgg ccaggctggt cttgaactga      1020
cctcaagtga tctgctcacc tcagctgcac aaagtgctgg gattacaggt gttagccaac      1080
caatacctg cctctattct cttgttaaga ggcatttagc atggttaata cagtctcttg      1140
ccctcataaa cagtgctggg aaggaaacac atgttcttgt gtatattgaa tgaaatttgt      1200
ttatacatta gatatttcca aatgttctct ttaagtactt cagtttacat cattactctc      1260
ctcctccctc ccctcccacc cccacccaca acagtattcc tcttttttcca tatccttgct      1320
aatgtttcaa agttttgctt tttacatttg ggtcttagat ccactagaat gtattttgc      1380
attgggatga agttgaaacc taatatattt tccaaatgag taaactgttg tcacagaact      1440
atttagttgt attacctcct ctcttgtata tcagatatat ctacatatat gtcagactgt      1500
ttctgggctg tctgtcctct ttaattagtt cgtgtatctg tttctgcatc agtagcatac      1560
tgtcttaact actgtagctt tataaagtct attgagtagg acaagtttgt ttcattcttc      1620
aaaattgctt tggctattct tggccctctg ctgtttcata ttaactttca gataaacttg      1680
tcaaattcta atgaaaactg ttgataaact tgttgattaa caaattctaa taaaaactgt      1740
tgagattttt attggaattg caatacattt atagattaac ggagaaagat attgacaata      1800
caattgagtt tccaattcac gaacatgtta tacctctcca ttaattcatg tcttttgaat      1860
gtatccacca atatggtttt gtaattttct tcataaagga catttaaaat tcttatttta      1920
agtgatctta tagttttatg ctaacgtgaa tgagattttt ccattatgtt tctgttggtt      1980
attcctgaag tggtaatgct tataattttg gggtgttggt cttgtatctg gcagcagata      2040
caagaggtgc tcagagttgt tcagggttgc tgaactctta gttctaaaag tgtctgtcat      2100
ttggggtttc tatgtagata atttaattat ctataaaaac agttcttcat ttcagttca       2160
tatatttcat attttcttaa gttttaattt ttatttttaa acacaattat ccataaaccc      2220
```

| | | | | |
|---|---|---|---|---|
| taacccttc | cctagtcaac | agcagtcaca | gccaaatgtt | ttattaattg ctatactcag | 2280 |
| tgtttcttgt | atctcatacc | ttctggggtt | tcttgtcttg | ttgaaataca cccttaatg | 2340 |
| tttctttagt | gaagacccaa | cagtggcact | cactcacctt | tgtttacctg aaaatttctt | 2400 |
| tattttcatc | ttaattcata | gtctgtcttt | tctccagtca | aggaagtgtc ttatagggaa | 2460 |
| gattctggtt | tcactatcgt | gtatccagga | tatatatgta | tttatagata gacttttaat | 2520 |
| ctgaggacta | atgtatttta | tcctacagta | ttaccaatca | ttatttcttc cataacttct | 2580 |
| agaccattcc | ttttgtactt | cttttttaga | gtccttatta | gatgagtgtt gactcttttc | 2640 |
| aatctagaca | tctttttaa | actatatttt | catactcttt | gtctctttag gtctgattt | 2700 |
| ttaagttcag | gggatatttc | attttgggtg | agttgtagca | ctacttcaat tcactaattc | 2760 |
| taattatatt | taatctacaa | gttattccat | ctataattta | tttcaattac cacttttgt | 2820 |
| tttcaaaatt | tctaattta | tatctgattt | tgtttcattt | ttgttttata atttcatgtt | 2880 |
| ctttctagat | tttacatctt | tttatgcata | ctaaacatac | tcacttgaaa gtctttgtaa | 2940 |
| gattgttcta | taaaatgtta | cctgaagtga | attc | | 2974 |

<210> SEQ ID NO 28
<211> LENGTH: 2987
<212> TYPE: DNA
<213> ORGANISM: Homo sapiens

<400> SEQUENCE: 28

| | | | | |
|---|---|---|---|---|
| ggatcccaat | aggagtcatt | aaaggcctgg | aaagtggtg | ccattaggag aaaaagaaat | 60 |
| gatttcttga | gcttgctctc | agttctcttt | taggctgtct | tgtactcagc agaatagtga | 120 |
| gatcttcaaa | ggttggggtt | tgatagtgcc | ttgaataatt | tttaacttta tattgccagc | 180 |
| ggaagaagca | ttctcttttt | agatttaaaa | aatgtagata | caaatattag gggttttatt | 240 |
| tttagtgaaa | catttcaaac | atacaggaat | agataattat | gtaatgaaca ctcgtatgtc | 300 |
| caccatctgg | ctttgtaaaa | tcttaaaatt | atgtcttatg | tgctcaattg ttttatttca | 360 |
| taaaagatac | tgataaacat | agctgaagtc | acttgtatac | cattcacctt cttccctgta | 420 |
| gattactatg | aactcggtct | ttttattctc | atacatattt | tttgtatttt tgcagtatat | 480 |
| ttatgtgttc | ataaacaata | tgtaattta | caatatgtaa | cacactagta acatactaat | 540 |
| ttaaaacttg | ttttagttt | acaatatgtt | gtaaactatt | gtaagctaaa gacatattgt | 600 |
| acaacctatt | gtaaaataaa | aacaggtttt | agttttaaat | taggtatgtt actgggatca | 660 |
| ttctgcaact | tgtttattcc | tctccagctt | tgattttgtg | gttttattat cttaacctac | 720 |
| acttttaatt | aatccatttt | atttgttaca | tggtattcta | ttatatcata aaaacttatc | 780 |
| tattctgttg | gtttttgttg | ttggtcattt | gagaccatgt | cttcgctctg tcacccaggc | 840 |
| tggagtacag | tggcgtgatc | ttggctcact | gtgacctctg | cctcccggat tcaagtggtt | 900 |
| ttggtgcctc | agcctcctga | gtagctggga | ttataggcgt | gtgccaccat gcccagctaa | 960 |
| tttttgtatt | tttaatagag | acgggatttc | accatgttgg | ccaggctggt cttgaactga | 1020 |
| cctcaagtga | tctgctcacc | tcagctgcac | aaagtgctgg | attacaggt gttagccacc | 1080 |
| atccctgcc | tctattctct | tgttaagagg | catttagcat | ggttatacag tctcttgccc | 1140 |
| tcataaacag | tgctggaaga | aacacatgtt | tcttgtgtat | atgaatgaaa atttgtttta | 1200 |
| tacattagat | atttccaaat | tgttctctta | agtacttcag | tttacatcat tactctcctc | 1260 |
| ctccctcccc | tcccacccc | acccacaaca | gtattcctct | ttttccatat ccttgctaat | 1320 |
| gtttctaaag | ttttgctttt | tacatttggg | tcttagatcc | actagaatgt attttgcat | 1380 |

-continued

```
tgggatgaag ttgaaaccta atatattttc caaatgagta aactgttgtc acagaactat   1440
ttagttgtat tacctcctct cttgtatatc agatatatct acatatatgt cagactgttt   1500
ctgggctgtc tgtcctcttt aattagttcg tgtatctgtt tctgcatcag tagcatactg   1560
tcttaactac tgtagcttta taaagtctat tgagtaggac aagtttgttt cattcttcaa   1620
aattgctttg gctattcttg gccctctgct gtttcatatt aactttcaga taaacttgtc   1680
aaattctaat gaaaactgtt gataaacttg ttgattaaca aattctaata aaaactgttg   1740
agatttttat tggaattgca atacatttat agattaacgg agaaagatat tgacaataca   1800
attgagtttc caattcacga acatgttata cctctccatt aattcatgtc ttttgaatgt   1860
atccaccaat atggttttgt aattttcttc ataaaggttt tacatttaaa aaattcttat   1920
ttttaagtga tcttatagtt tttattgcta atgtgaatga ttttttttc cattatgttt   1980 ctgttggtta ttcctgaagt ggtaatgctt ataattttgg ggtgttggtc ttgtatctgg   2040
cagcagatac aagaggtgct cagagttgtt cagggttgct gaactcttag ttctaaaagt   2100
gtctgtcatt tggggtttct atgtagataa tttaattatc tataaaaaca gttcttcatt   2160
ttcagttcat atatttcata tttctttaag ttttaatttt tattttttaaa cacaattatc   2220 cataaaaccc taaccctttc cctagtcaac agcagtcaca gccaaatgtt ttattaattg   2280
ctatactcag tgtttcttgt atctcatacc ttctgggggtt tcttgtcttg ttgaaataca   2340
ccctttaatg tttctttagt gaagacccaa cagtggcact cactcacctt tgtttacctg   2400
aaaatttctt tattttcatc ttaattcata gtctgtcttt tctccagtca aggaagtgtc   2460
ttatagggaa gattctggtt tcactatgct gtatccaggg atatatatgt atttatagat   2520
agacttttaa tctgaggact aatgtatttt atcctacagt attaccaatc attatttctt   2580
ccataacttc tagaccattc cttttgtact tcttttttag agtccatatta gatgagtgtt   2640 gacactttc aatctagaca tctttttttaa actatatttt catactcttt gtctctttag   2700
gtctgatttt ttaagttcag gggaatattt cattttgggt gagttgtagc actcacttcc   2760
aattcactaa ttctaattat atttaatcta caagttattc catctataat ttatttcaat   2820
taccactttt tgttttcaaa atttctaatt ttatatctga ttttgtttca ttttgttttt   2880
ataatttcat gttctttcta gattttacat ctttttatgc atactaaaca tactcacttg   2940
aaagtctttg taagattgtt ctataaaatg ttacctgaag tgaattc                 2987
```

<210> SEQ ID NO 29
<211> LENGTH: 33
<212> TYPE: DNA
<213> ORGANISM: artificial
<220> FEATURE:
<223> OTHER INFORMATION: olignonucleotide
<220> FEATURE:
<221> NAME/KEY: misc_feature
<222> LOCATION: (7)..(11)
<223> OTHER INFORMATION: n is a, c, g, or t
<220> FEATURE:
<221> NAME/KEY: misc_feature
<222> LOCATION: (18)..(22)
<223> OTHER INFORMATION: n is a, c, g, or t
<220> FEATURE:
<221> NAME/KEY: misc_feature
<222> LOCATION: (29)..(33)
<223> OTHER INFORMATION: n is a, c, g, or t

<400> SEQUENCE: 29

```
attttannnn nattttannn nnattttann nnn                                33
```

```
<210> SEQ ID NO 30
<211> LENGTH: 33
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, c, g, or t
<220> FEATURE:
<221> NAME/KEY: misc_feature
<222> LOCATION: (18)..(22)
<223> OTHER INFORMATION: n is a, c, g, or t
<220> FEATURE:
<221> NAME/KEY: misc_feature
<222> LOCATION: (29)..(33)
<223> OTHER INFORMATION: n is a, c, g, or t

<400> SEQUENCE: 30
taaaatnnnn ntaaaatnnn nntaaaatnn nnn                                33

<210> SEQ ID NO 31
<211> LENGTH: 28
<212> TYPE: DNA
<213> ORGANISM: artificial
<220> FEATURE:
<223> OTHER INFORMATION: oligonucleotide

<400> SEQUENCE: 31
attttagctc gatttagct cgatttta                                      28

<210> SEQ ID NO 32
<211> LENGTH: 33
<212> TYPE: DNA
<213> ORGANISM: artificial
<220> FEATURE:
<223> OTHER INFORMATION: oligonucleotide

<400> SEQUENCE: 32
attttagctc gatttagct cgatttagc tcg                                 33

<210> SEQ ID NO 33
<211> LENGTH: 28
<212> TYPE: DNA
<213> ORGANISM: artificial
<220> FEATURE:
<223> OTHER INFORMATION: olignonucleotide

<400> SEQUENCE: 33
taaaatcgag ctaaaatcga gctaaaat                                     28

<210> SEQ ID NO 34
<211> LENGTH: 33
<212> TYPE: DNA
<213> ORGANISM: artificial
<220> FEATURE:
<223> OTHER INFORMATION: oligonucleotide

<400> SEQUENCE: 34
taaaatcgag ctaaaatcga gctaaaatcg agc                               33

<210> SEQ ID NO 35
<211> LENGTH: 264
<212> TYPE: PRT
<213> ORGANISM: Escherichia coli

<400> SEQUENCE: 35
```

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
        50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
                195                 200                 205

Cys Gly Arg Leu Gly Val Ala Asp Arg Tyr Gln Asp Ile Ala Leu Ala
210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 36
<211> LENGTH: 795
<212> TYPE: DNA
<213> ORGANISM: artificial
<220> FEATURE:
<223> OTHER INFORMATION: polynucleotide

<400> SEQUENCE: 36

| | | |
|---|---|---|
| atgattgaac aagatggatt gcacgcaggt tctccggccg cttgggtgga gaggctattc | 60 |
| ggctatgact gggcacaaca gacaatcggc tgctctgatg ccgccgtgtt ccggctgtca | 120 |
| gcgcagggc gcccggttct ttttgtcaag accgacctgt ccggtgccct gaatgaactg | 180 |
| caagacgagg cagcgcggct atcgtggctg gccacgacgg gcgttccttg cgcagctgtg | 240 |
| ctcgacgttg tcactgaagc gggaagggac tggctgctat gggcgaagt gccggggcag | 300 |
| gatctcctgt catctcacct tgctcctgcc gagaaagtat ccatcatggc tgatgcaatg | 360 |
| cggcggctgc atacgcttga tccggctacc tgcccattcg accaccaagc gaaacatcgc | 420 |
| atcgagcgag cacgtactcg gatggaagcc ggtcttgtcg atcaggatga tctggacgaa | 480 |
| gagcatcagg ggctcgcgcc agccgaactg ttcgccaggc tcaaggcgag catgcccgac | 540 |

```
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacacgcgt tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795
```

<210> SEQ ID NO 37
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (5)..(10)
<223> OTHER INFORMATION: n is a, c, g, or t
<400> SEQUENCE: 37

```
aaaannnnn                                                            10
```

<210> SEQ ID NO 38
<211> LENGTH: 11
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (5)..(11)
<223> OTHER INFORMATION: n is a, c, g, or t
<400> SEQUENCE: 38

```
aaaannnnn n                                                          11
```

<210> SEQ ID NO 39
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (6)..(10)
<223> OTHER INFORMATION: n is a, c, g, or t
<400> SEQUENCE: 39

```
aaaaannnnn                                                           10
```

<210> SEQ ID NO 40
<211> LENGTH: 11
<212> TYPE: DNA
<213> ORGANISM: artificial
<220> FEATURE:
<223> OTHER INFORMATION: olignonucleotide
<220> FEATURE:
<221> NAME/KEY: misc_feature
<222> LOCATION: (6)..(11)
<223> OTHER INFORMATION: n is a, c, g, or t
<400> SEQUENCE: 40

```
aaaaannnnn n                                                         11
```

<210> SEQ ID NO 41
<211> LENGTH: 10
<212> TYPE: DNA

```
<213> ORGANISM: artificial
<220> FEATURE:
<223> OTHER INFORMATION: oligonucleotide
<220> FEATURE:
<221> NAME/KEY: misc_feature
<222> LOCATION: (7)..(10)
<223> OTHER INFORMATION: n is a, c, g, or t

<400> SEQUENCE: 41 aaaaaannnn                                                                10

<210> SEQ ID NO 42
<211> LENGTH: 11
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, c, g, or t

<400> SEQUENCE: 42
aaaaaannnn n                                                              11

<210> SEQ ID NO 43
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (5)..(10)
<223> OTHER INFORMATION: n is a, c, g, or t

<400> SEQUENCE: 43 ttttnnnnnn                                                                10

<210> SEQ ID NO 44
<211> LENGTH: 11
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (5)..(11)
<223> OTHER INFORMATION: n is a, c, g, or t

<400> SEQUENCE: 44
ttttnnnnnn n                                                              11

<210> SEQ ID NO 45
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (6)..(10)
<223> OTHER INFORMATION: n is a, c, g, or t

<400> SEQUENCE: 45 tttttnnnnn                                                                10

<210> SEQ ID NO 46
<211> LENGTH: 11
```

```
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (6)..(11)
<223> OTHER INFORMATION: n is a, c, g, or t

<400> SEQUENCE: 46
tttttnnnnn n                                                              11

<210> SEQ ID NO 47
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(10)
<223> OTHER INFORMATION: n is a, c, g, or t

<400> SEQUENCE: 47 tttttnnnn                                                                 10

<210> SEQ ID NO 48
<211> LENGTH: 11
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, c, g, or t

<400> SEQUENCE: 48 tttttnnnn n                                                               11

<210> SEQ ID NO 49
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(10)
<223> OTHER INFORMATION: n is a, c, g, or t

<400> SEQUENCE: 49 taaaatnnnn                                                                10

<210> SEQ ID NO 50
<211> LENGTH: 11
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, c, g, or t

<400> SEQUENCE: 50
taaaatnnnn n                                                              11

<210> SEQ ID NO 51
```

```
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (8)..(10)
<223> OTHER INFORMATION: n is a, c, g, or t

<400> SEQUENCE: 51 taaaaatnnn                                                                  10

<210> SEQ ID NO 52
<211> LENGTH: 11
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (8)..(11)
<223> OTHER INFORMATION: n is a, c, g, or t

<400> SEQUENCE: 52
taaaaatnnn n                                                                11

<210> SEQ ID NO 53
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (9)..(10)
<223> OTHER INFORMATION: n is a, c, g, or t

<400> SEQUENCE: 53 taaaaaatnn                                                                  10

<210> SEQ ID NO 54
<211> LENGTH: 11
<212> TYPE: DNA
<213> ORGANISM: artificial
<220> FEATURE:
<223> OTHER INFORMATION: olignonucleotide
<220> FEATURE:
<221> NAME/KEY: misc_feature
<222> LOCATION: (9)..(11)
<223> OTHER INFORMATION: n is a, c, g, or t

<400> SEQUENCE: 54
taaaaaatnn n                                                                11

<210> SEQ ID NO 55
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(10)
<223> OTHER INFORMATION: n is a, c, g, or t

<400> SEQUENCE: 55 attttannnn                                                                  10
```

```
<210> SEQ ID NO 56
<211> LENGTH: 11
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(11)
<223> OTHER INFORMATION: n is a, c, g, or t

<400> SEQUENCE: 56
attttannnn n                                                              11

<210> SEQ ID NO 57
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (8)..(10)
<223> OTHER INFORMATION: n is a, c, g, or t

<400> SEQUENCE: 57 attttttannn                                                               10

<210> SEQ ID NO 58
<211> LENGTH: 11
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (8)..(11)
<223> OTHER INFORMATION: n is a, c, g, or t

<400> SEQUENCE: 58 attttttannn n                                                             11

<210> SEQ ID NO 59
<211> LENGTH: 10
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (9)..(10)
<223> OTHER INFORMATION: n is a, c, g, or t

<400> SEQUENCE: 59 atttttttann                                                               10

<210> SEQ ID NO 60
<211> LENGTH: 11
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (9)..(11)
<223> OTHER INFORMATION: n is a, c, g, or t

<400> SEQUENCE: 60 atttttttann n                                                             11
```

<210> SEQ ID NO 61
<211> LENGTH: 34
<212> TYPE: DNA
<213> ORGANISM: artificial
<220> FEATURE:
<223> OTHER INFORMATION: oligonucleotide

<400> SEQUENCE: 61
ccagctaact gctatacaca atagacattt gtgc    34

<210> SEQ ID NO 62
<211> LENGTH: 40
<212> TYPE: DNA
<213> ORGANISM: artificial
<220> FEATURE:
<223> OTHER INFORMATION: oligonucleotide

<400> SEQUENCE: 62
ctgccaacag taattagcac atgaattcac ttcaggtaac    40

<210> SEQ ID NO 63
<211> LENGTH: 24
<212> TYPE: DNA
<213> ORGANISM: artificial
<220> FEATURE:
<223> OTHER INFORMATION: oligonucleotide

<400> SEQUENCE: 63
gtgcctgact tgaactgcaa tggg    24

<210> SEQ ID NO 64
<211> LENGTH: 23
<212> TYPE: DNA
<213> ORGANISM: artificial
<220> FEATURE:
<223> OTHER INFORMATION: oligonucleotide

<400> SEQUENCE: 64
cagtaattag cacatgaatt cac    23

<210> SEQ ID NO 65
<211> LENGTH: 36
<212> TYPE: DNA
<213> ORGANISM: artificial
<220> FEATURE:
<223> OTHER INFORMATION: oligonucleotide

<400> SEQUENCE: 65
ggtcttgtat ctgcctagga gatacaagag gtgctc    36

<210> SEQ ID NO 66
<211> LENGTH: 36
<212> TYPE: DNA
<213> ORGANISM: artificial
<220> FEATURE:
<223> OTHER INFORMATION: oligonucleotide

<400> SEQUENCE: 66
gagcacctct tgtatctcct aggcagatac aagacc    36

<210> SEQ ID NO 67
<211> LENGTH: 40
<212> TYPE: DNA
<213> ORGANISM: artificial
<220> FEATURE:
<223> OTHER INFORMATION: oligonucleotide

<400> SEQUENCE: 67
catagcgttg gctaccgctg atatcgctga agagcttggc                          40

<210> SEQ ID NO 68
<211> LENGTH: 40
<212> TYPE: DNA
<213> ORGANISM: artificial
<220> FEATURE:
<223> OTHER INFORMATION: oligonucleotide

<400> SEQUENCE: 68
gccaagctct tcagcgatat cagcggtagc caacgctatg                          40

<210> SEQ ID NO 69
<211> LENGTH: 40
<212> TYPE: DNA
<213> ORGANISM: artificial
<220> FEATURE:
<223> OTHER INFORMATION: oligonucleotide

<400> SEQUENCE: 69
catagcgttg gctaccgttg atatcgctga agagcttggc                          40

<210> SEQ ID NO 70
<211> LENGTH: 40
<212> TYPE: DNA
<213> ORGANISM: artificial
<220> FEATURE:
<223> OTHER INFORMATION: oligonucleotide

<400> SEQUENCE: 70
gccaagctct tcagcgatat caacggtagc caacgctatg                          40

<210> SEQ ID NO 71
<211> LENGTH: 44
<212> TYPE: DNA
<213> ORGANISM: artificial
<220> FEATURE:
<223> OTHER INFORMATION: oligonucleotide

<400> SEQUENCE: 71
ctatcaggac atagcgttgg gatcccgtga tattgctgaa gagc                     44

<210> SEQ ID NO 72
<211> LENGTH: 44
<212> TYPE: DNA
<213> ORGANISM: artificial
<220> FEATURE:
<223> OTHER INFORMATION: oligonucleotide

<400> SEQUENCE: 72
gctcttcagc aatatcacgg gatcccaacg ctatgtcctg atag                     44

<210> SEQ ID NO 73
<211> LENGTH: 42
<212> TYPE: DNA
<213> ORGANISM: artificial
<220> FEATURE:
<223> OTHER INFORMATION: oligonucleotide

<400> SEQUENCE: 73
ggacatagcg ttggctacac gcgttattgc tgaagagctt gg                       42

<210> SEQ ID NO 74

```
<211> LENGTH: 42
<212> TYPE: DNA
<213> ORGANISM: artificial
<220> FEATURE:
<223> OTHER INFORMATION: oligonucleotide

<400> SEQUENCE: 74
ccaagctctt cagcaataac gcgtgtagcc aacgctatgt cc                            42

<210> SEQ ID NO 75
<211> LENGTH: 33
<212> TYPE: DNA
<213> ORGANISM: artificial
<220> FEATURE:
<223> OTHER INFORMATION: curved origin motif

<400> SEQUENCE: 75
aaaatcgagc taaaatcgag ctaaaatcga gct                                     33
```